(12) United States Patent
Kalovidouris et al.

(10) Patent No.: US 7,858,578 B2
(45) Date of Patent: Dec. 28, 2010

(54) METHODS OF INDUCING NEURONAL GROWTH BY A FUCOSE-α(1-2) GALACTOSE (FUC-α(1-2) GAL) MOIETY AND A LECTIN

(75) Inventors: Stacey Kalovidouris, Houston, TX (US); Cristal I. Gama, Los Angeles, CA (US); Linda C. Hsieh-Wilson, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 641 days.

(21) Appl. No.: 11/297,165

(22) Filed: Dec. 7, 2005

(65) Prior Publication Data

US 2006/0177413 A1    Aug. 10, 2006

Related U.S. Application Data

(60) Provisional application No. 60/635,730, filed on Dec. 10, 2004, provisional application No. 60/683,823, filed on May 23, 2005.

(51) Int. Cl.
| | |
|---|---|
| *A61K 38/00* | (2006.01) |
| *A61K 49/00* | (2006.01) |
| *G01N 33/53* | (2006.01) |
| *C12N 5/08* | (2006.01) |
| *C12N 5/00* | (2006.01) |
| *C12N 5/06* | (2006.01) |

(52) U.S. Cl. .......................... 514/2; 435/7.21; 435/368; 435/366; 424/9.1

(58) Field of Classification Search ....................... None
See application file for complete search history.

(56) References Cited

PUBLICATIONS

The definition of lectin in the Stedman's Medical Dictionary 27th edition, (1 page).*
Smalla et al. NeuroReport. 1998. 9:813-817.*
Walsh et al. Annu. Rev. Cell Dev. Biol. 1997. 13: 425-56.*
Luthi et al. J. Neurochem. 1991. 56: 1493-1498.*
,Berezovskaya et al. J. Neurosci. Res. 1995. 42: 192-8.*
Farmer et al. J. Neurobiol. 1992. 23: 354-63.*
Ducray et al. Neurosci. Lett. 1999. 274: 17-20.*
Ngasaki et al. Biomacromelecules. 2001. 2:1067-1070.*
Kim et al. J. Neurosci. 2003, 23: 10703-10709.*
Shin et al. Exp. Mol. Med. Dec. 31, 2002; 34: 401-410.*
Ferreira et al. Molecular Medicine, 1998. 4: 22-28.*
Alonso et al., "Lectin histochemistry shows fucosylated glycoconjugates in the primordial germ cells of Xenopus embryos," J. Histochem. Cytochem. (2003) 51:239-243.
Brown et al., "Combining chondrocytes and smooth muscle cells to engineer hybrid soft tissue constructs," Tissue Engr. (2000) 6:297-305.
Bullock et al., "Effect of the amnesic agent, 2-deoxygalactose, on incorporation of fucose into chick brain glycoproteins," J. Neurochem. (1990) 54:135-142.
Daly and Ziff, "Post-transcriptional regulation of synaptic vesicle protein expression and the developmental control of synaptic vesicle formation," J. Neurosci. (1997) 17:2365-2375.
Gill et al., "Direct brain infusion of glial cell line-derived neurotropic factor in Parkinson disease," Nature Med. (2003) 9:589-595.
Haselhorst et al., "Molecular recognition of sialyl Lewis$^x$ and related saccharides by two lectins," J. Am. Chem. Soc. (2001) 123:10705-10714.
Hilfiker et al., "Synapsis as regulators of neurotransmitter release," Phil. Trans. R. Soc. London B (1999) 354:269-279.
Holden et al., "Structure and function of enzymes of enzymes of the Leloir pathway for galactose metabolism," J. Biol. Chem. (2003) 278:43885-43888.
Horch et al., "Cultured human keratinocytes on type I collagen membranes to reconstitute the epidermis," Tissue Engr. (2000) 6:53-67.
Huttner et al., "Synapsin I (Protein I), a nerve terminal-specific phosphoprotein. III. Association with synaptic vesicles studied in a highly purified synaptic vesicle preparation," J. Cell. Biol. (1983) 96:1374-1388.
Jork et al., "Monoclonal antibody specific for histo-blood group antigens H (types 2 and 4) interferes with long-term memory formation in rats," Neurosci. Res. Comm. (1991) 8:21-27.
Jork et al., "Identification of Rat Hippocampal Glycoproteins Showing Changed Fucosylation Following 2-deoxy-d-galactose-induced amnesia in a brightness discrimination task," Neurosci. Res. Comm. (1989) 5:105-110.
Kao et al., "A third member of the synapsin gene family," Proc. Natl. Acad. Sci. USA (1998) 95:4667-4672.
Karsten et al., "A new monoclonal antibody (A46-B/B10) highly specific for the blood group H type 2 epitope: generation, epitope analysis, serological and histological evaluation," Br. J. Cancer (1988) 58:176-181.
Krug et al., "The amnesic substance 2-deoxy-D-galactose suppresses the maintenance of hippocampal LTP," Brain Res. (1991) 540:237-242.
Lorenzini et al., "2-Deoxy-D-galactose effects on passive avoidance memorization in the rat" Neurobiol. Learn. Mem. (1997) 68:317-324.
Matsui et al., "Surface glycosyltransferase activities during development of neuronal cell cultures," J. Neurochem. (1986) 46:144-150.

(Continued)

*Primary Examiner*—Christine J Saoud
*Assistant Examiner*—Chang-Yu Wang
(74) *Attorney, Agent, or Firm*—Isaac M. Rutenberg; Bozicevic, Field & Francis LLP

(57) ABSTRACT

Fucose galactose carbohydrates have been shown to induce neuronal outgrowth. The invention includes methods of inducing neuronal outgrowth using carbohydrates, assemblies, and polymers bearing fucose-galactose moieties, as well as associated proteins. Cell growth can be stimulated in cells in culture or in cells within an animal or patient. Growth stimulation has application to understanding and treatment of neurodegenerative diseases including, for example, Parkinson's disease, Alzheimer's disease and multiple sclerosis and conditions such as stroke, brain injury and spinal cord injury. Such compounds, polymers, and assemblies also can be used to increase neural stem or progenitor cells in culture or in an animal, and to enervate engineered tissue.

6 Claims, 18 Drawing Sheets
(14 of 18 Drawing Sheet(s) Filed in Color)-

PUBLICATIONS

Matthies et al., "Fucose and fucosylgalactose enhance in vitro hippocampal long-term potentiation," Brain Res. (1996) 725:276-280.

McCabe et al., "Passive avoidance training increases fucose incorporation into glycoproteins in chick forebrain slices in vitro," Neurochem. Res. (1985) 10:1083-1095.

Pohle et al., "Incorporation of [$^3$H] fucose in rat hippocampal structures after conditioning by perforant path stimulation and after LTP-producing tetanization," Brain Res. (1987) 410:245-256.

Popov et al., "Changes in activities of fucokinase and fucosyltransferase in rat hippocampus after acquisition of a brightness discrimination reaction," Pharmacol. Biochem. Behav. (1983) 19:43-47.

Rose et al., "Long term memory formation in chicks is blocked by 2-deoxygalactose, a fucose analog," Behav. Neural Biol. (1987) 48:246-258.

Ryan et al., "Synaptic vesicle recycling in syapsin I knock-out mice," J. Cell. Biol. (1996) 134:1219-1227.

Schwartz et al., "Isolation and characterization of neural progenitor cells from post-mortem human cortex," J. Neurosci. Res. (2003) 74:838-851.

Sudhof et al., "Synapsins: mosaics of shared and individual domains in a family of synaptic vesicle phosphoproteins," Science (1989) 245:1474-1480.

Svendsen and Langston,"Stem cells for Parkinson disease and ALS: replacement or protection," Nature Med. (2004) 10:224-225.

Toma, "Precise targeting in Parkinson's," The Scientist (2003), .thescientist.com/news/20030331/03.

Valtorta et al., "Accelerated structural maturation induced by synapsina I at developing neuromuscular synapses of Xenopus laevis," Eur. J. Neurosci. (1995) 7:261-270.

Vermeer et al., "Fucosylation of linear alcohols: a study of parameters influencing the stereochemistry of glycosylation," Eur. J. Org. Chem. (2001) 2001:193-203.

Waugh, "Artificial skin for patient use," Massachusettes Institute of Technology News Office, 1996, web.mit.edu/newsoffice/1996.

Worthington Biochemical Corporation, Concanavalin A_Worthington Biochemical Product Catalog, Abstract only, found at www.worthington-biochem.com/CONA/cat.html (2008).

* cited by examiner

SYNTHESIS OF III

METHODS OF INDUCING NEURONAL GROWTH BY A FUCOSE-α(1-2) GALACTOSE (FUC-α(1-2) GAL) MOIETY AND A LECTIN

CROSS REFERENCE TO RELATED APPLICATION

This application claims priority under 35 U.S.C. §119(e)(1) to Provisional U.S. Patent Application Ser. No. 60/635,730, filed Dec. 10, 2004, and Provisional U.S. Patent Application Ser. No. 60/683,823, filed May 23, 2005, which are incorporated herein by reference in their entirety.

FEDERAL SUPPORT STATEMENT

This invention was made with government support under grant number RO1 NS045061 awarded by the NIH. The government has certain rights in the invention.

FIELD OF THE INVENTION

This invention relates to compounds and methods for inducing neuronal growth involving compounds having one or more fucose-galactose moieties.

BACKGROUND

Neuronal growth and differentiation is important in a wide variety of processes from neuronal development to memory. The ability to modulate such growth and differentiation is important for the study of neurons as well as for the treatment of diseases and conditions that involve neuronal growth, degradation, or injury. For example, many neurodegenerative diseases, such as Alzheimer's Disease and Huntington's Disease, are characterized by the death of neurons. Traumatic injuries to nerves, including trauma to the spine and damage caused by ischemic cerebral stroke, can involve neuronal death. Any of these conditions can potentially be treated using agents that promote growth of neurons. Additionally, the generation of long-term memory is believed to result from strengthening of neuronal connections and synaptic remodeling.

Fucoseα(1-2) galactose (abbreviated herein as Fucα(1-2)Gal), which exists as a terminal carbohydrate modification to N- and O-linked glycoproteins, has been implicated in modulating neuronal processes such as learning and memory. For instance, preventing formation of Fucα(1-2)Gal linkages by incorporation of 2-deoxy-D-galactose (2-dGal) into glycan chains has been shown to cause reversible amnesia in animals. (Bullock, S. et al., *J. Neurochem.*, 54:135-142 (1990); Rose, S. P. R., et al., *Behav. Neural Biol.*, 48:246-258 (1987); Lorenzini, C. G. A. et al., *Neurobiol. Learn. Mem.*, 68:317-324 (1997)). 2-dGal also interferes with the maintenance of long-term potentiation (LTP), a form of synaptic plasticity that is closely associated with learning and memory. (Krug, M., et al., *Brain Res.*, 540:237-242 (1991)). Moreover, injection of a monoclonal antibody specific for Fucα(1-2)Gal has been found to impair memory formation in animals, presumably by blocking the Fucα(1-2)Gal epitope (Karsten, U., et al., *Br. J. Cancer* 58:176-181 (1988); Jork, R., et al., *Neurosci. Res. Comm.* 8:21-27 (1991)).

The fucosylation of neuronal proteins may be regulated in response to synaptic activity. Both task-specific learning and LTP have been shown to induce the fucosylation of proteins at the synapse (McCabe, N. R., et al., *Neurochem. Res.*, 10:1083-1095 (1985); Pohle. W., et al., *Brain Res.*, 410:245-256 (1987)). Notably, addition of exogenous fucose or 2'fucosyllactose was found to enhance LTP in hippocampal slices (Matthies, H., et al., *Brain Res.*, 725:276-280 (1996)). Furthermore, the activity of fucosyltransferases, enzymes involved in the transfer of fucose into glycoproteins, has been demonstrated to increase substantially during synaptogenesis (Matsui, Y., et al., *J. Neurochem.*, 46:144-150 (1986)) and upon passive avoidance training in animals (Popov, N., et al., *Pharmacol. Biochem. Behav.*, 19:43-47 (1983)). These results suggest that the fucosylation of certain neuronal proteins may be highly regulated in the brain and contribute to synaptic plasticity. Despite these intriguing observations, little is known about the molecular mechanisms by which Fucα(1-2)Gal sugars influence neuronal communication processes. Surprisingly, no Fucα(1-2)Gal glycoproteins have been characterized from the brain, and the precise roles of the sugars in regulating the structure and function of neuronal proteins is presently unclear.

A need exists for a product and process for modulating neuronal processes such as learning and memory. Furthermore, a need exists for a product and a process for modulating neuronal cell growth, which is, among other functions, involved in modulating learning and memory and recovery from neuronal disorders or damage. An additional need exists for a compound and method to improve growth of neural stem cells.

SUMMARY OF THE INVENTION

In one embodiment, the invention provides methods and compounds for inducing or stimulating neuronal growth. In a preferred embodiment, a neuron is contacted with a compound having a fucose-galactose moiety and/or its associated proteins. Preferably, the moiety is a Fucα(1-2)Gal moiety. The methods and compounds are used to induce neuronal growth and/or to treat neuronal CNS disorders or damage, such as neurodegenerative disease, ischemic cerebral stroke, and physical trauma.

In another embodiment, a lectin specific to a fucose-galactose compound is used to induce or stimulate neuronal growth by contacting the neuron with the lectin.

Also provided are methods for identifying compounds that interact with a cellular receptor that is specific for a fucose-galactose moiety. The compound may be a modified form of a fucose-galactose compound, a small molecule, or any other compound that meets the criteria.

The compound can be identified, for example, by a direct or indirect competition assay with Fucα(1-2)Gal, a binding assay with a molecule such as a particular lectin that specifically binds Fucα(1-2)Gal moieties, or by an immunological assay.

In a preferred embodiment, the compound has a fucose-galactose moiety, including but not limited to Fucα(1-2)Gal. The fucose-galactose moiety can exist in a variety of forms, including but not limited to as a small molecule, attached to oligomers or polymers, and/or in assemblies having one or more fucose-galactose moieties.

In another preferred embodiment, fucose-galactose compounds that induce neuronal growth are isolated. These compounds are selected for their similarity in binding characteristics and/or immunological characteristics to known fucose-galactose compounds that induce growth. The identified fucose-galactose compounds are used to induce neuronal growth and/or to treat neuronal CNS disorders or damage, such as neurodegenerative disease, ischemic cerebral stroke, and physical trauma.

Likewise, in another preferred embodiment, lectins that specifically bind fucose-galactose compounds are isolated.

The identified lectins are used to induce neuronal growth and/or to treat neuronal CNS (central nervous system) and PNS (peripheral nervous system) disorders or damage, such as neurodegenerative disease, ischemic cerebral stroke, spinal cord injuries, and physical trauma.

In a further embodiment, fucose containing saccharides are used to induce growth of neural stem cells. These cells are cultured in vitro, followed by implantation into a mammalian CNS. Specific compounds that induce the best growth are isolated. The neural stem cells are used to treat neuronal brain disorders including, but not limited to, Parkinson's disease and Alzheimer's disease, as well as PNS disorders including, but not limited to, spinal cord injuries.

In another embodiment, a method for improving the engineering of tissue for transplantation to a mammal is provided. Compounds of the invention are applied to the tissue to increase enervation and to promote neurite extension.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
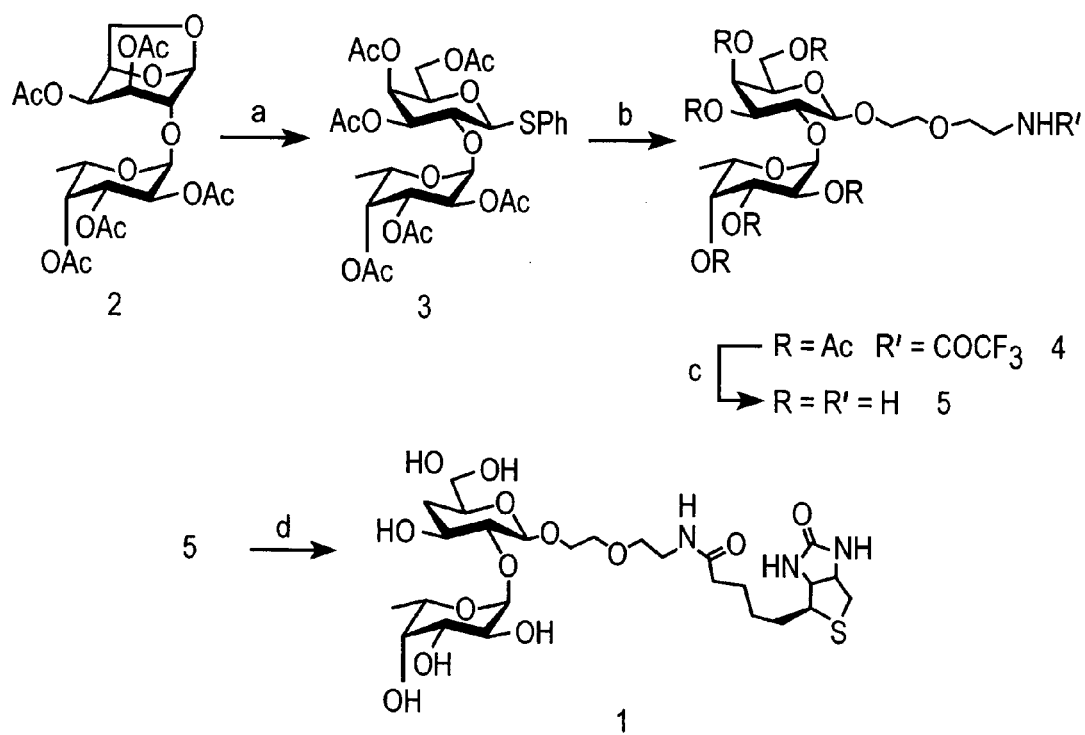
FIG. 1. Synthesis scheme for compound III (Fucα(1-2) Gal).

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature As used in this specification and the appended claims, the singular forms "a", "an" and "the" include plural referents unless the context clearly dictates otherwise. Thus, for example, reference to "a fucose-galactose compound" includes a single fucose-galactose compound as well as a combination or mixture of two or more different fucose-galactose compounds.

The present invention provides compositions and methods for the treatment of neuronal CNS disorders or damage, such as neurodegenerative disease, ischemic cerebral stroke, and physical trauma in mammals. Also provided are compositions and methods to induce growth of neurites and modulate neuronal morphology. Fucose-galactose compounds, and in particular, Fucα(1-2)Gal, have been found to act on neurons to induce growth. This ability can be used for a variety of purposes and in a variety of manners. As learning and memory are associated with the functions that are disclosed herein as being modulated by fucose-galactose compounds, fucose-galactose compounds have been found to be useful in stimulating learning and memory through development of hippocampal neurons and growth of their neurites. They have been found to specifically bind to neuronal lectins, thereby affecting neuronal communication.

Compounds and Compositions

The term "fucose-galactose moiety" is used herein to describe Fucα(1-2)Gal moieties as well as compounds that mimic Fucα(1-2)Gal in their ability to bind to lectins specific for binding glycoproteins having a Fucα(1-2)Gal-containing carbohydrate modification. Lectins are proteins of non-immune origin that interact with sugar molecules with varying degrees of specificity, without modifying them. For example, the lectins *Lotus tetragonolobus* agglutinin (LTL) and *Ulex europaeus* I agglutinin (UEA-I) interact preferentially with terminal Fucα(1-2)Gal carbohydrates. Other lectins bind strongly to other fucose-galactose disaccharide groups; for example, *Anguilla anguilla* (AAA) has strong affinity for terminal Fucα(1-3) or Fucα(1-4) linkages as well as Fucα(1-6)GlcNAc residues in N-glycans. (Alonso, E., et al., *J. Histochem. Cytochem.*, 51:239-243 (2003)) In a preferred embodiment the fucose-galactose moiety has the structure shown below as compound I.

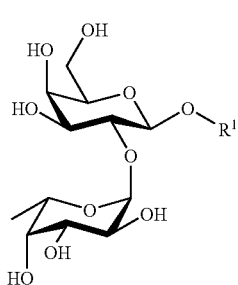

(I)

R1 can be substituted in general with a chemical functionality, including but not limited to an alkyl chain, polymer, peptide, imaging agent such as quantum dot or fluorescence dye, photoactivatable group, or affinity capture agent such as biotin. Substitutions other than at the R1 position are included in the invention provided that the resultant compound binds Fucα(1-2)Gal-binding lectins specifically.

The fucose-galactose-containing molecules have been found to bind specifically to lectins that attach to the cell surface of particular neurons, at the synapse, and to cause growth of the neurons. It is a specific interaction, in that other, related moieties, such as Fucα(1-3)Gal and Fucα(1-3)Glc do not have the same effects on neurons. On the other hand, lectins that specifically bind Fucα(1-2)Gal also cause growth of neurons. For the first time, receptors in the brain have been identified that bind specifically to Fucα(1-2)Gal.

Lectins that are included in the invention include but are not limited to those that contain specific fucose-galactose receptors. When these lectins are applied to hippocampal neurons, the neurons undergo the same type of structural change, including increase in number, and extension in length, of neurites as result from the application of the fucose-galactose moieties themselves. Examples of known lectins that contain specific fucose-galactose receptors include the agglutinins UEA-I and LTL. Any lectin or portion of a lectin that specifically binds fucose-galactose moieties can be used in the present invention.

Additional agents that mimic the binding properties of fucose-galactose moieties can also be used. These agents can be identified by a number of methods, including through a competitive binding assay or an immunological assay. In an example of a competitive binding assay, a test compound is provided in solution with a solid phase binding molecule that is specific for fucose-galactose-containing carbohydrates. Increasing amount of fucose-galactose moieties are added, and competition between the compound and the fucose-galactose moieties for the binding molecule is measured as a decrease in binding of the test compound to the solid phase. This can be followed with a physical analysis of the effects of the test compound on a neuron. For example, a cell or tissue is contacted with a putative fucose-galactose like compound. The characteristics of the cell are assessed, including cell viability, morphology, proliferation, apoptosis, activation of specific genes, etc. In another embodiment, potential ligands to the binding partner can be identified using labeled antibodies or lectins known to bind fucose-galactose moieties, including, for example, UEA-I or LTL agglutinins, in a competition assay for a solid phase fucose-galactose moiety.

Polymers and Assemblies

The invention includes compositions that include a multitude of fucose-galactose moieties that are either covalently or non-covalently assembled. Suitable approaches for multivalent drug delivery include those reviewed, for example, in Seok-Ki Choi, SYNTHETIC MULTIVALENT MOLECULES: CONCEPTS AND BIOMEDICAL APPLICATIONS, Wiley, 2004. In one embodiment, the fucose-galactose moieties are appended to a polymer chain to form glycopolymers. In certain embodiments, the glycopolymers contains between about 2 and about 1,000 pendant saccharide moieties.

Polymers having fucose-galactose moieties can be synthesized using a variety of techniques. In one embodiment, a polymerizable group is appended to the fucose-galactose moiety. When the fucose-galactose moiety has the structure I, the polymerizable group is preferably attached at the R1 position. In another embodiment, a polymer has a repeated reactive group. In yet another embodiment, a polymer has a variety of reactive side groups, including but not limited to electrophiles, nucleophiles, and photoactivatable crosslinkers. In a related embodiment, a polymer has side groups useful for signaling and detection, such as quantum dots. Fucose-galactose moieties having a complementary reactive group can be reacted with any of these types of polymers.

Polymers for use with the invention can be linear or branched. Preferred are dendrimers that provide attachment sites on substantially all surfaces. Attachment of the fucose-galactose moieties to the polymer is preferably accomplished without decreasing the functionality of the moieties, including their ability to bind lectins and receptors. The invention also includes non-covalent and other assemblies that have more than one fucose-galactose moiety. The multivalent polymer backbones can also contribute to the formation of aggregates of fucose-galactose moieties by, for example, forming a scaffold that brings the moieties in proximity to each other. These associations of moieties can induce aggregation of fucose-galactose binding proteins, such as lectins.

A schematic view of one embodiment of a polymer bearing multiple fucose-galactose moieties is shown in structure II.

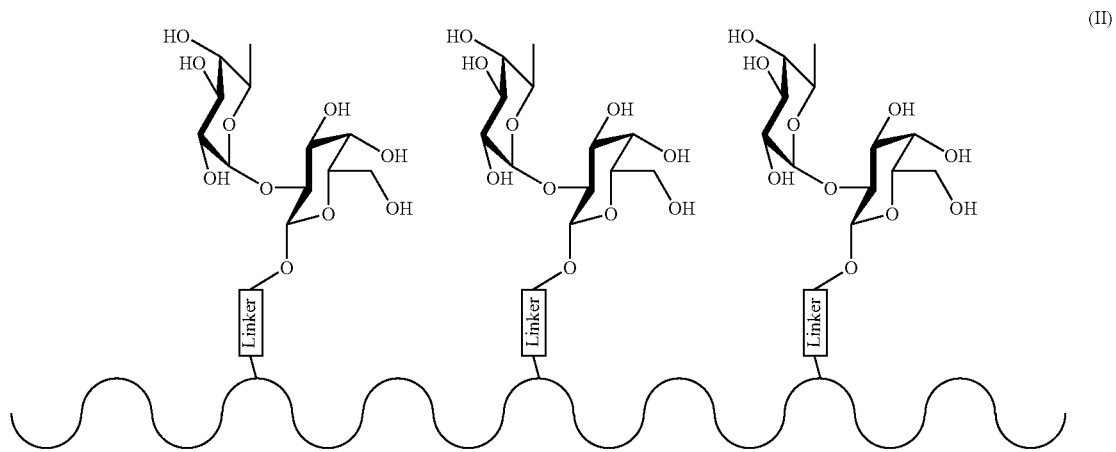

(II)

The fucose-galactose moieties attached to a backbone may be the same or different. In one embodiment, the fucose-galactose moieties are tailored to react with the desired neuron or lectin. In a preferred embodiment, the fucose-galactose moiety is Fucα(1-2)Gal, as in structure II. The polymer is selected from, but not limited to, a polyacrylamide, polyethylene glycol, polypropylene glycol, polypeptide, polyamine, polyamidoamine, polymers generated via ring-opening metathesis, carbohydrate-based polymers, hydrophilic polymers such as HPMA (poly(N-(2-hydroxypropyl)methacrylamide)), and hydrogels. The polymer is preferably readily derivatized with the carbohydrate, relatively water-soluble, non-immunogenic, and biocompatible. Preferably, it provides stability for the fucose-galactose moieties, and can allow a stronger binding between the fucose-galactose moieties and a binding partner, such as a receptor or lectin.

Methods of Use

Fucose-galactose compounds, along with their receptors and the lectins that are specific for these compounds, can be used to treat a variety of conditions that involve improper growth of, degeneration of, or damage to neurons in a mammal, especially neuronal CNS and PNS disorders or damage, such as neurodegenerative and other diseases, ischemic cerebral stroke, and physical trauma. The term "trauma" as used herein includes damage caused by a physical blow to the head or spinal column. As used herein, "disease" includes neurodegenerative diseases as well as infections such as those that cause hydrocephaly, e.g., viral encephalitis caused by infections of agents such as HIV. Examples of neurodegenerative diseases that can be treated with the invention include, but are not limited to, Alzheimer's disease, Parkinson's disease, Lou Gehrig's disease (Amyotrophic Lateral Sclerosis), Multiple Sclerosis, Huntington's disease, and other neurodegenerative diseases and conditions where neurons have been compromised.

As used herein, "compromised" means that the neuron has less than normal function, which includes but is not limited to shortening or loss of dendrites, shortened half-life, decreased number of synapses, decreased amount of glycosylation, inability to grow, abnormal morphology, and cell death. According to the methods of the invention, a therapeutically effective amount of a fucose-galactose-containing compound, or functional substitute or modification thereof, including polymers, assemblies and the like, is administered to a patient. The compound can be administered to the site of the injury or diseased tissue, can be delivered by intrathecal injection, or with appropriate formulation can be administered systemically. In one embodiment, a fucose-galactose compound, such as Fucα(1-2)Gal-PAA, is delivered directly to the region of the brain where the damaged neurons reside. In another embodiment, the composition is delivered to the CNS such as through the spinal column. In yet another embodiment, the composition is delivered to the PNS by injection next to one or more neurons in need of treatment.

The fucose-galactose compounds and lectins can also be used to increase neuronal communication by causing growth of neurites. The neurites can interact with other neurons, increasing the paths of communication. This increases learning and memory by increasing the plasticity of synapses. The compositions of this invention can be applied to the brain of a mammal in need thereof in order to treat certain learning disabilities or memory loss. The compound is administered as described below.

The compounds of the invention, including fucose-galactose-containing compounds and their associated proteins, can be used in the culture of neurons in vitro for transplanting into a mammalian brain. NPCs ("neural stem cells" or "multipotent neural precursors") are fairly undifferentiated neural cells that have the capacity to develop into many different specialized neurons. NPCs can be cultured from pathogen-negative crude cortex homogenates in a base medium such as high glucose 1:1 DMEM:F12 (Irvine Scientific, Irvine, Calif.), supplemented with 10% heat-inactivated fetal bovine serum, 10% BIT 9500 (Stem Cell Technologies), 40 ng/ml basic FGF-2 (Invitrogen, La Jolla, Calif.), 20 ng/mL EGF (Invitrogen), and 20 ng/mL PDGF-AB (Peprotech) on fibronectin-coated dishes. See Schwartz, P. H., et al., *J. Neuro. Res.*, 74:838-851 (2003). According to the methods of the invention, a fucose-galactose-containing compound, or functional substitute or modification thereof, including polymers, assemblies and the like, is added to the culture medium in an amount sufficient to induce neuronal growth and neurite elongation. The amount is in the range of about 500 nM to about 500 mM, preferably between about 1 μM and about 500 μM, and can be determined by cell culture procedures known to those of skill in the art.

According to the methods of the invention, the compounds of the invention, including those containing fucose-galactose moieties, can be used to improve tissue engineering. Tissue, such as skin, is grown in culture for transfer to a patient in need as a skin graft. The addition of one or more of the compounds of the invention to the culture medium increases enervation of the skin. In one embodiment, immature neurons are added to keratinocyte cultures, and grown in normal tissue culture media in the presence of Fucα(1-2)Gal to enhance growth of the neurons. Fucα(1-2)Gal is supplied at a concentration of about 500 nM to about 500 mM, preferably about 1 μM to about 500 μM. The appropriate concentration can be empirically determined by standard methods known in the art.

The resulting tissue is more natural in that feeling and other normal neuronal communications and responses are provided by the neurons.

EXAMPLES

General Methods:

Chemicals were purchased from commercial suppliers and used as received. Lectins were purchased from Vector Labs (Burlingame, Calif.), polymers from GlycoTech (Gaithersburg, Md.), and tissue culture reagents from Gibco (Carlsbad, Calif.). Unless stated otherwise, reactions were performed in flame-dried glassware under an argon environment, using freshly distilled solvents. Thin-layer chromatography (TLC) was carried out on glass sheets coated with Kieselgel 60 F254 Fertigplatten (Merck, Darmstadt, Germany). The plates were inspected by UV light and developed by treatment with a cerium ammonium molybdate stain followed by heating. Column chromatography was carried out using silica gel 60 (ICN Silitech 32-63 D, 60 Å). High-resolution fast atom bombardment mass spectra (FAB-MS) were obtained on a Jeol JMS-600H spectrometer, and low-resolution electrospray mass spectra (ES-MS) were acquired on a PE Sciex API 365 LC/MS/MS Triple Quadrupole mass spectrometer with a proton nanospray source. $^1$H and $^{13}$C NMR spectra were recorded using a Varian Mercury 300 spectrometer with the residual solvent or TMS as the internal standard. Data for 1H are reported as follows: chemical shift (δ ppm), multiplicity (s=singlet, d=doublet, t=triplet, q=quartet, m=multiplet), coupling constant in Hz, and integration.

Example 1

Synthesis of Compound 1 (Biotinylated Fucα(1-2)Gal)

Compound III, biotinylated Fucα(1-2)Gal, was synthesized as follows and as shown in FIG. 1, for use as a probe for molecules that bind Fucα(1-2)Gal.

Phenyl 3,4,5-tri-O-(2,3,4-tri-O-acetyl-α-L-fucopyranosyl)-1-thio-β-D-galactopyranoside (3): The following thioglycoside formation procedure was adapted from a method reported by Motawia and coworkers. (Motawia, M. S., et al., *J. Carbohydr. Res.* 252:69-84 (1994)). Known compound 2 (Wegmann, B., et al., *Carbohydr. Res.* 184:254-261 (1988)) (1.80 g, 3.40 mmol), (phenylthio)trimethylsilane (2.0 mL, 10.4 mmol) and zinc iodide (3.30 g, 10.4 mmol) in $CH_2Cl_2$ (20.0 mL) were stirred at rt for 21 h. The mixture was diluted with EtOAc (120 mL) and washed successively with saturated aqueous $NaHCO_3$ (150 mL), water (3×50 mL) and brine (20 mL). The organic layer was then dried over sodium sulfate, filtered and concentrated in vacuo. The residue was dissolved in dry THF (15.0 mL) and 1 M tetrabutylammonium fluoride in THF (6.0 mL) was added. After this reaction mixture stirred for an additional 20 min at rt, the solvent was evaporated. Thereafter, the residue was redissolved in EtOAc (60 mL), washed with water (3×30 mL), saturated aqueous $NaHCO_3$ (30 mL) and brine (30 mL), dried over $Na_2SO_4$, then filtered and concentrated to afford the β-thioglycoside (1.6 g, 76%). To a solution of the β-thioglycoside (310 mg, 0.50 mmol) in dry pyridine (6.0 mL) was added acetic anhydride (3.0 mL). The reaction was allowed to stir at rt overnight. The solvent was evaporated and residual pyridine was azeotroped with toluene. Column chromatography ($SiO_2$, Hexane/EtOAc, 3:1) afforded 3 (330 mg, quant.). 1H NMR (300 MHz, CDCl3): δ=1.12 (d, 3H, J=6.5 Hz, H-6'), 1.51 (s, 3H, OAc), 1.66 (2s, 6H, OAc), 1.76 (s, 3H, OAc), 1.87 (s, 3H, OAc), 1.93 (s, 3H, OAc), 3.41 (ddd, 1H, J=0.8 Hz, 7.0 Hz, 7.3 Hz, H-5), 3.83 (dd, 1H, J=7.7 Hz, H-1), 4.06 (dd, 1H, J=7.3 Hz, 10.2 Hz, H-6b), 4.12 (dd, 1H, J=7.7 Hz, J=10 Hz, H-2), 4.13 (dd, 1H, J=7.0 Hz, 10.2 Hz, H-6a), 4.62 (dq, 1H, J=1.1 Hz, 6.5 Hz, H-5'), 5.19 (dd, 1H, J=3.5 Hz, 10 Hz, H-3), 5.42 (dd, 1H, J=0.8 Hz, 3.5 Hz, H-4), 5.44 (dd, 1H, J=3.8 Hz, 11.0 Hz, H-2'), 5.60 (dd, 1H, J=1.1 Hz, 3.4 Hz, H-4'), 5.74 (d, 1H, J=3.8, H-1'), 5.83 (dd, 1H, J=3.4 Hz, 11.0 Hz, H-3'), 7.20-7.59 (m, 5H, Ph); 13C NMR (75 MHz, CDCl3): δ=15.9, 20.7 (3C), 20.8 (3C), 61.8, 65.8, 67.3, 67.9, 68.1, 70.1, 71.0, 73.1 (3C), 87.8, 98.2, 100.2, 127.7, 129.3, 131.7, 133.2, 169.9, 170.0, 170.2, 170.5, 170.6, 170.6. HRMS m/z Calculated for C30H38O15NaS [M+Na]+693.1253. Found 693.1271.

2-(2-Trifluoroacetamido ethoxy)ethyl-3,4,5-tri-O-(2,3,4-tri-O-acetyl-α-L-fucopyranosyl)-1 -β-D-galactopyranoside (4): The following is a modified procedure from Kanie et al., *Tet. Lett.*, 37:4551-4554 (1996). Compound 3 (330 mg, 0.50 mmol) was azeotroped with toluene and then dissolved in $CH_2Cl_2$ (5.0 mL) and 2-(2-trifluoroacetamido ethoxy) ethanol (67 mg, 0.30 mmol) containing molecular sieves (4 Å). After stirring for 10 min, the mixture was cooled to 20° C. N-Iodosuccinimide (107 mg, 0.40 mmol), followed by silver triflate (108 mg, 0.40 mmol), was added. The reaction was allowed to warm to rt and proceeded for 2 h after addition of the silver triflate. After the reaction was complete, it was diluted with $CH_2Cl_2$ and filtered. The filtrate was washed with saturated aqueous $Na_2SO_4$, filtered, and concentrated. Column chromatography ($SiO_2$, Hexane/EtOAc, 3:1) afforded 4 (210 mg, 68%, α:β=1:3): only β was used. 1H-NMR (300 MHz, CDCl$_3$): δ 1.10 (d, 3H, J=6.5 Hz, H-6'), 1.99 (s, 3H, OAc), 2.00 (s, 3H, OAc), 2.01 (s, 3H, OAc), 2.04 (s, 3H, OAc), 2.13 (s, 3H, OAc), 2.15 (s, 3H, OAc), 3.40 (ddd, 3H, J=0.8 Hz, 7.0 Hz, 7.3 Hz, H-5, OCH$_2$), 3.55-3.78 (m, 6H, OCH$_2$), 3.88 (dd, 1H, J=7.8 Hz, H-1), 3.97 (dd, 1H, J=7.8 Hz, 10.2 Hz, H-6b), 4.02 (dd, 1H, J=7.8, 10.0 Hz, H-2), 4.14 (dd, 1H, J=7.8 Hz, 10.2 Hz, H-6a), 4.28 (m, 1H, H-3'), 4.50 (dq, 1H, J=1.1 Hz, 6.5 Hz, H-5'), 5.00 (dd, 1H, J=3.6 Hz, 10.0 Hz, H-3), 5.32 (dd, 1H, J=0.5 Hz, 3.3 Hz, H-4), 5.31-5.42 (m, 3H, H-2', H-4', H-1'), 7.49 (bs, 1H, N—H); 13C NMR (75 MHz, CDCl3): δ=16.3, 21.0 (2C), 28.7, 29.7, 45.5, 61.8, 65.0, 66.2, 67.9, 68.2 (2C), 69.4, 69.7, 70.3, 70.6, 71.0, 71.4, 97.9, 98.5, 128.6 (2C), 129.5 (2C), 130.1 (2C), 132.4, 170.1, 170.2, 170.4. HRMS m/z Calculated for C30H42F3NO18 [M+H]+ 762.2465. Found 762.2470.

(N-[6-([Biotinoyl]amino)ethoxy)ethyl-O-(α-L-fucopyranosyl)-(1-2)-β-D-galactopyranoside (1): The procedure for the preparation of 5 was adapted from Newman, H., *J Org Chem.*, 30:1287-1288(1965). Compound 4 (0.50 g, 0.70 mmol) was dissolved in a 7% solution of $K_2CO_3$ in aqueous MeOH (2:5, vol:vol), and the reaction mixture was stirred for 12 h at rt. The solution was neutralized with 1N HCl, and the organic layer was extracted with MeOH and concentrated to afford 5 (270 mg, quant.) as a white foam. Amine 5 (70 mg, 0.17 mmol) was dissolved in DMF (2.0 mL), and the pH was adjusted to 9 using TEA. N-Hydroxysuccinimido biotin (70 mg, 0.20 mmol) was added and the reaction stirred for 12 h at rt. The reaction mixture was concentrated to afford an off-white syrup. Preparative reversed-phase chromatography using a gradient of 0% to 50% aqueous 0.1% TFA in $CH_3CN$ over 60 min followed by a gradient of 50% to 100% $CH_3CN$ over 60 min (retention time 40 min; flow rate 21 mL/min) afforded pure 1 (60 mg) in 60% yield. $^1H$ NMR (300 MHz, $D_2O$): δ 1.05 (d, 3H, J=6.6 Hz, H–6'), 1.23-1.31 (m, 2H, $CH_2$), 1.41-1.60 (m, 4H, $CH_2$), 2.12 (t, 2H, J=7.0 Hz, $CH_2$), 2.62 (d, 2H, J=13.2 Hz, $SCH_2$), 2.84 (dd, 2H, J=4.8 Hz, 12.6 Hz, $CH_2$), 3.17 (m, 4H, $CH_2$), 3.23 (dd, 2H, J=4.8 Hz, J=8.7 Hz, $CH_2$), 3.42-4.10 (m, 12H, H–2, H–3, H–4, H–5, H–6a, H–6b, H–2', H–3', H–4', H–5', CH), 4.45 (d, 1H, J=7.8 Hz, H–1), 4.46 (m, 1H, CH), 5.08 (d, 1H, J=2.2 Hz, H–1'); 13C NMR (75 MHz, $D_2O$): δ=15.6, 25.1, 27.7 (2C), 27.9, 35.4 (2C), 39.0, 39.7, 55.4, 60.2, 61.1, 62.1, 66.8, 67.2, 68.3, 68.8, 69.3, 69.4, 70.8, 71.7, 77.9, 98.2, 101.6, 165.3, 176.9. HRMS m/z Calculated for C26H45N3O13S [M+H]+640.2751. Found 640.2725.

Example 2

Identification of Neuronal Lectin Receptors

It was hypothesized that the Fucα(1-2)Gal moiety could be interacting with a lectin receptor in the brain. As no such proteins had been reported, compound III was used to probe for the presence of potential Fucα(1-2)Gal specific lectin receptors in neurons.

Hippocampal neurons were cultured using a procedure modified from Goslin and Banker, in Culturing Nerve Cells, Banker, G., Goslin, K., Eds., pp. 251-281, MIT Press: Cambridge, Mass. 1991. Briefly, the hippocampi of embryonic day 18 (E18) rats were dissected and transferred to 4.5 mL of ice-cold Calcium and Magnesium Free-Hank's Balanced Salt Solution (CMF-HBSS). Trypsin (2.5%, no EDTA) was added to 5 mL, and the tissue was incubated for 15 min at 37° C. The trypsin solution was removed and the tissue sample washed three times with 5 mL of CMF-HBSS. Cells were then dissociated from the tissue in 1 mL of CMF-HBSS by passing through a P1000 pipet tip twenty times. The cells were counted, diluted into Minimal Eagle's Medium (MEM) plus 10% fetal bovine serum, and seeded on poly-DL-ornithine-coated glass coverslips (Carolina Biological) at a density of 75 cells/mm2 (100 µL/coverslip) for 30 min. After this time, 500 µL of supplemented Neurobasal medium (47.5 mL Neurobasal medium without Lglutamine; 0.5 mL L-glutamine (200 mM); 0.5 mL penicillin/streptomycin (10,000 U/mL); 0.5 mL antibiotic-antimycotic (100× stock), 1.0 mL B-27 serum-free supplement (50× stock); 50 µL of 0.5 M kynurenic acid in 1 N NaOH) was added to each coverslip. The use of kynurenic acid to block glutamate receptor ion channels and enhance neuronal health and survival is standard protocol for neuronal cultures. Id. The cultures were maintained in 5% $CO_2$ at 37° C. in supplemental Neurobasal medium.

Figure 2:
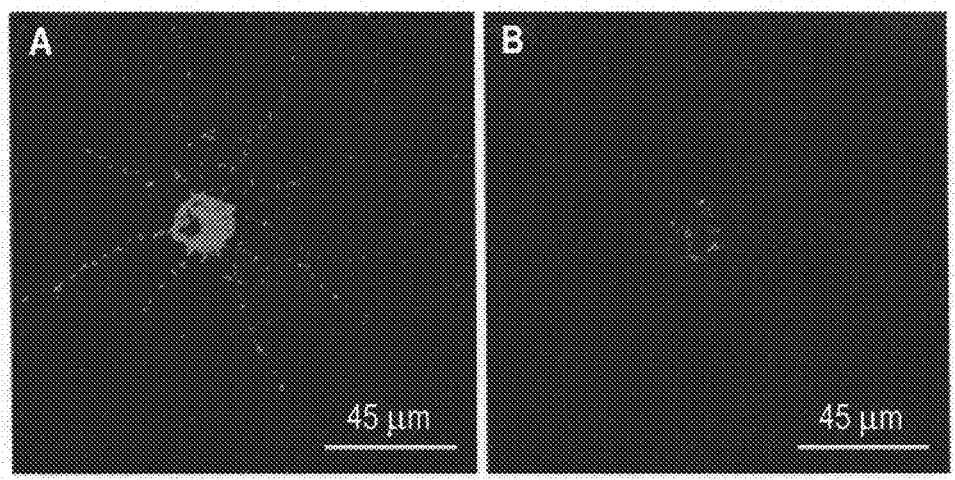
FIG. 2. Compound III binds to embryonic day 18 (E18) hippocampal neurons. Immunofluorescence images of neurons (23 days in vitro) after treatment with 3 mM of (A) compound III or (B) biotin in the presence of 10 μM PAO.

After 23 days in culture, the medium was replaced, and neurons were treated with the endocytosis inhibitor phenylarsine oxide (PAO; 4 µL in DMSO, final concentration 10 µM) (Nouel, D., et al., *J. Neurosci.* 17:1795-1803 (1997)) and either compound III (24 µL in PBS, final concentration 3 mM), or biotin (24 µL in PBS, final concentration 3 mM), in supplemented Neurobasal medium (400 µL final volume) for 1 h at 37° C., 5% $CO_2$. After 1 h, neurons were rinsed 2 times with PBS, fixed in 4% paraformaldehyde for 20 min at rt, washed 2 times with PBS, permeabilized in 0.3% Triton X-100 for 5 min at rt, and washed 2 times with PBS. Non-specific binding was blocked with 3% BSA for 1 h at rt and then rinsed one time with PBS. Compound III was detected with streptavidin conjugated to AlexaFluor 488 (1:200, Molecular Probes). Dye-conjugated streptavidin was added in 3% BSA for 1 h at 37° C. and the excess reagent washed off 5 times with PBS. Coverslips were then mounted onto slides with Vectashield, sealed, and imaged using confocal laser microscopy. Results can be seen in FIG. 2. Panel A shows binding of compound III to the cell body and neurite processes of hippocampal cells, whereas panel B shows that this binding is not between the biotin moieties and the neuron.

Figure 3:
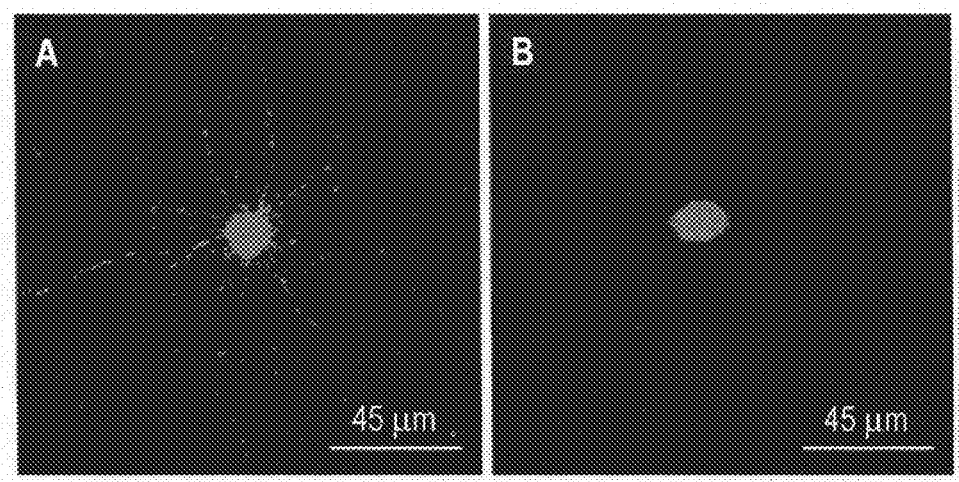
FIG. 3. Lipid extraction of neurons does not alter the labeling with probe III. E18 hippocampal neurons (23 days in vitro) were de-lipidated with MeOH/CHCl, prior to labeling with 3 mM of (A) III or (B) biotin in the presence of 10 μM phenylarsine oxide (PAO). Scale bars represent 45 μm.

When the cellular membranes were de-lipidated prior to treatment with compound III, labeling was not diminished, indicating that compound III bound to protein. De-lipidation was performed on some samples following the protocol of Yavin, E. et al., *J. Neurosci. Res.* 9:229-237 (1983). Briefly, after 23 days in culture, cells were rinsed once with PBS then exposed to MeOH/CHCl$_3$ (½ by vol.) for 15 min at –80° C. This procedure fixes the cells to the coverslip and extracts cellular lipids. After removing the MeOH/CHCl$_3$ mixture, coverslips were dried at rt then incubated with 3% BSA for 1 hr at rt. After one rinse with PBS, neurons were treated with PAO and the procedure described above was followed. FIG. 3 shows the same results as FIG. 2, after removal of lipids. FIG. 3A, like 2A, shows a well-defined neuronal cell body and many neurites, while FIG. 3B shows the same minor binding of the biotin alone to the cell body but not the neurites.

Example 3

Demonstration of Neuronal Response With a Fucα(1-2)Gal Polymer

The association of Fucα(1-2)Gal with potential lectins was studied to determine if it would stimulate neuronal growth. As carbohydrates have weak binding affinities for lectins ($K_{assoc}=10^3-10^6M$), (Schmid, R.-S., et al., *J. Neurosci.,* 20:4177-4188 (2000)) we used polyacrylamide polymers bearing multiple Fucα(1-2)Gal epitopes (FucGal-PAA; MW ~30 kDa, 20% GlycoTech, Gaithersburg, Md.) to enhance the interaction. All experiments were performed in duplicate. Polymers with 20% density were used for part A, while 10%, 20%, or 30% disaccharide density were used for part B. Hippocampal neurons were cultured as described above. After treatment with kynurenic acid, media was removed, and 50 µL solution of carbohydrate-PAA conjugate in PBS or a 50 µL solution of lectin (3.7 µM) in HEPES was added to supplemented Neurobasal medium (450 µL) on each coverslip. The cultures were incubated in 5% $CO_2$ at 37° C. and analyzed.

The hippocampal neurons on the coverslips were rinsed one time with PBS, fixed in 4% paraformaldehyde for 20 min at rt, washed twice with PBS, permeabilized in 0.3% Triton X-100 for 5 min at rt, and washed twice with PBS. Cells were then incubated with anti-tau antibodies (rabbit polyclonal, 1:600; Sigma) in 3% BSA for 2 h at rt. Excess antibody was rinsed away 5 times with PBS. The secondary antibody, anti-rabbit IgG AlexaFluor 488 (1:600; Molecular Probes), was added for 1 h at 37° C. in 3% BSA. Excess secondary antibody was washed off 5 times with PBS. The coverslips were mounted onto glass slides using Vectashield mounting medium (Vector Labs) and sealed with clear nail polish. Cells were imaged using a Zeiss Axiovery 100 M inverted laser microscope (Biological Imaging Center in the Beckman Institute at Caltech). Images were captured with LSM Pascal software using a 40× plan-neofluar oil objective and an excitation wavelength of 488 nm or 568 nm.

For each experiment, 50 randomly selected cells were analyzed per coverslip using similar quantitative analysis techniques reported by Schmid et al., *J. Neurosci.* 20:4177-4188 (2000). Briefly, only neurites longer than ~10 µm and not in contact with other cells were measured using NIH Image 1.62 software. The mean neurite lengths were compared among the different conditions by the ANOVA test using the statistical analysis program StatView (SAS Institute Inc., Cary, N.C.).

Figure 4A:
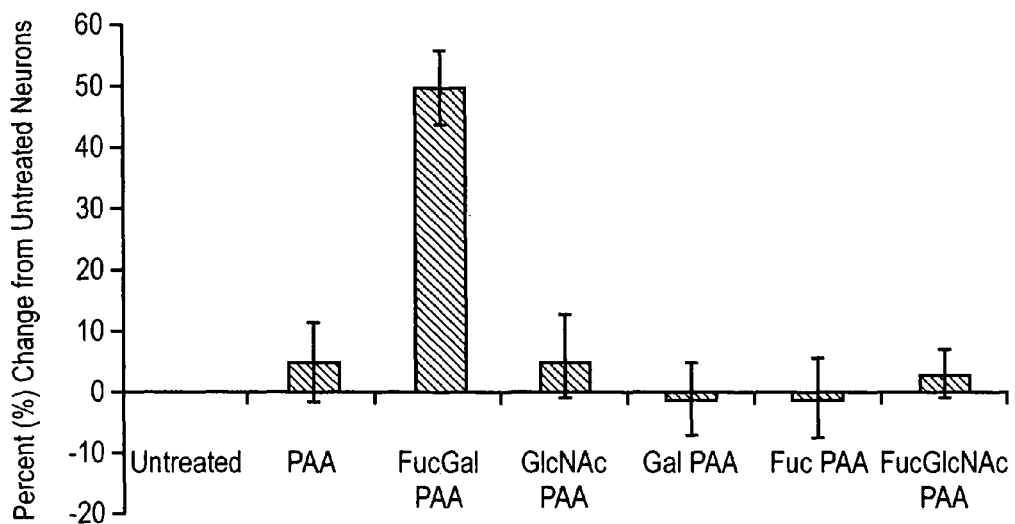
FIG. 4. (A) Fucα(1-2)Gal promotes neuronal growth. Neurite outgrowth was analyzed quantitatively by measuring the longest neurite per cell after treatment with the indicated compounds (130 μM. Error bars represent SEM from 100 total neurons in two separate experiments. (B) Neurite outgrowth activity increases with the Fucα(1-2)Gal concentration and polymer valency. Disaccharide residue concentrations are reported. p values are relative to the untreated neurons.

FIG. 4 shows distinct and specific growth responses to Fucα(1-2)Gal. In FIG. 4A, FucGal-PAA shows the percent change of the treated cells as compared to untreated neurons for a variety of carbohydrate-PAA compounds. Neurons treated with FucGal-PAA for 24 h exhibited striking changes in cellular morphology: the length of the major neurite extension was increased by 50±6% relative to the untreated control, as can be seen in FIG. 4A. A polymer lacking the disaccharide (PAA) had no significant effect, indicating that Fucα(1-2)Gal was responsible for the growth-inducing activity.

The specificity of the reaction was analyzed by comparing the results using FucGal-PAA to those when using polymers bearing different carbohydrate epitopes. Polymers containing N-acetylglucosamine (GlcNAc-PAA) or D-galactose (Gal-PAA) failed to promote neuronal growth. L-fucose-bearing polymers, such as L-fucose PAA (Fuc-PAA) and Fucα(1-3) GlcNAc PAA (FucGlcNAc-PAA), displayed neuronal processes similar to those of untreated cells, indicating that the galactose moiety of Fucα(1-2)Gal may be an important contributor to lectin binding and/or activation. Together, these findings demonstrate that the observed neuritogenic activity is specific for Fucα(1-2)Gal.

Figure 4B:
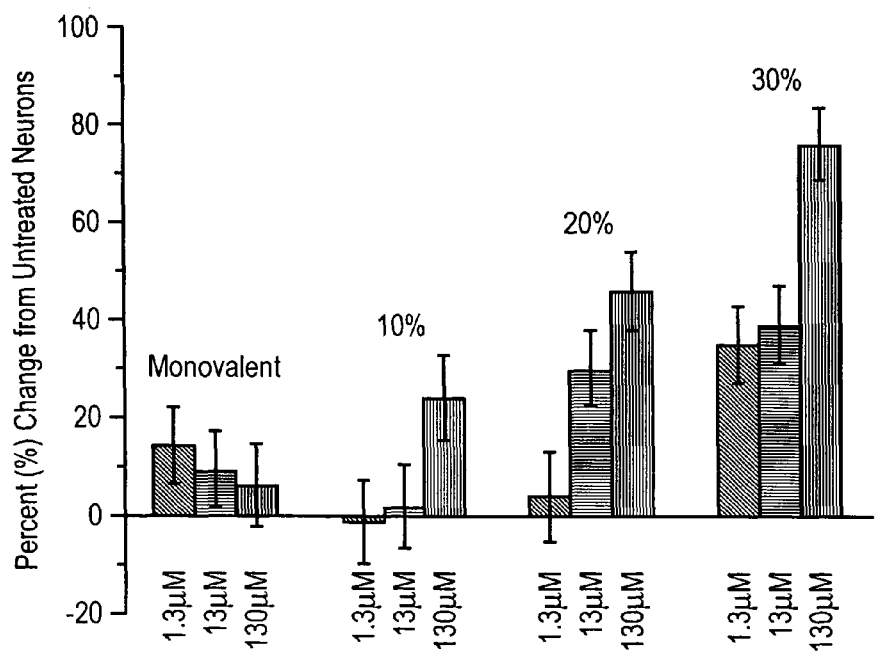

FIG. 4B shows that neurite growth increases with concentration of carbohydrate-PAA conjugate, as well as with increase in valency of the fucose-galactose moieties on the carbohydrate. The growth-promoting activity of each FucGal PAA polymer increased as the concentration of disaccharide increased. In addition, the potency of the compounds was dramatically enhanced with increasing carbohydrate valency, with the 20% density polymer stimulating growth by 76±8%. In contrast, monovalent ligand 1 showed only modest activity even though it was capable of binding to neurons. These results suggest that the multivalent PAA scaffold promotes the interaction of Fucα(1-2)Gal with lectin receptors and may facilitate their assembly into higher-order complexes. The ability of multivalent ligands to enhance binding affinity and cluster lectins has been observed in other systems. (Nouel, D., et al., *J. Neurosci.*, 17:1795-1803 (1997)). Without intent to limit the scope of the invention, it is proposed that the multivalent ligands may be working by enhancing binding affinity and clustering lectins.

Example 4

Glycoproteins Covalently Modified by Fucα(1-2)Gal

Hippocampal neurons were analyzed for the presence of Fucα(1-2)Gal modified glycoproteins by their ability to bind the lectin UEA-I. Hippocampal neuronal cultures were prepared as described above and maintained at 37° C., 5% $CO_2$ in supplemented Neurobasal medium. After 23 days in culture, the medium was replaced, and neurons were treated with the endocytosis inhibitor phenylarsine oxide (PAO; 4 µL in DMSO, final concentration 10 µM) and fluorescein-conjugated UEA-I lectin (4 µL, 1:100 final dilution) in supplemented Neurobasal medium (400 µL final volume) for 1 h at 37° C., 5% $CO_2$. After 1 h, neurons were rinsed 2 times with PBS, fixed in 4% paraformaldehyde for 20 min at rt, washed 2 times with PBS, permeabilized in 0.3% Triton X-100 for 5 min at rt, and washed 2 times with PBS. Non-specific binding was blocked with 3% BSA for 1 h at rt and then rinsed one time with PBS. Anti-tau antibody (rabbit polyclonal, 1:600; Sigma) was added in 3% BSA for 2 h at rt and the excess antibody rinsed off 5 times with PBS. Anti-tau was detected with a secondary antibody conjugated to AlexaFluor 568 (goat anti-rabbit IgG, 1:600; Molecular Probes). The secondary antibodies were added in 3% BSA for 1 h at 37° C. and the excess reagent washed off 5 times with PBS. Coverslips were then mounted onto slides with Vectashield, sealed, and imaged using confocal laser microscopy.

Figure 5A:
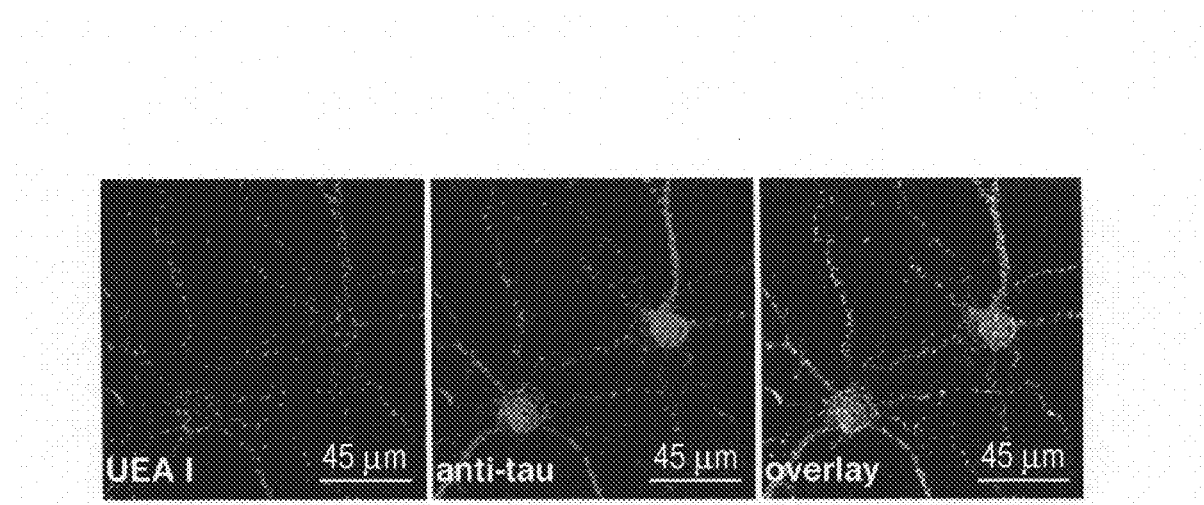
FIG. 5. Selectivity of Fucα(1-2)Gal for neurite growth. (A) Co-staining of hippocampal neurons (23 days in vitro) with UEA-I lectin (green) and an anti-tau antibody (red) in the presence of 10 μM PAO. Lipid extraction using MeOH/CHCl$_3$ did not diminish the labeling. (B) Quantitative analysis of neurite length after treatment with the indicated lectins (3.7 μM) was measured. Only Fucα(1-2)Gal-selective lectins stimulate neurite outgrowth. Error bars represent SEM from 100 total neurons in two separate experiments.

As shown in FIG. 5A, Fucα(1-2)Gal glycoproteins are indeed present and display a punctate staining consistent with localization to synapses. The first box shows binding of UEA-I; the second shows location of neurons as identified by binding to anti-tau antibody. The overlay in box 3 shows the coincidence of binding, indicating that UEA-I is binding to the neurons, and that Fucα(1-2)Gal moieties are present on the neurons.

Figure 5B:
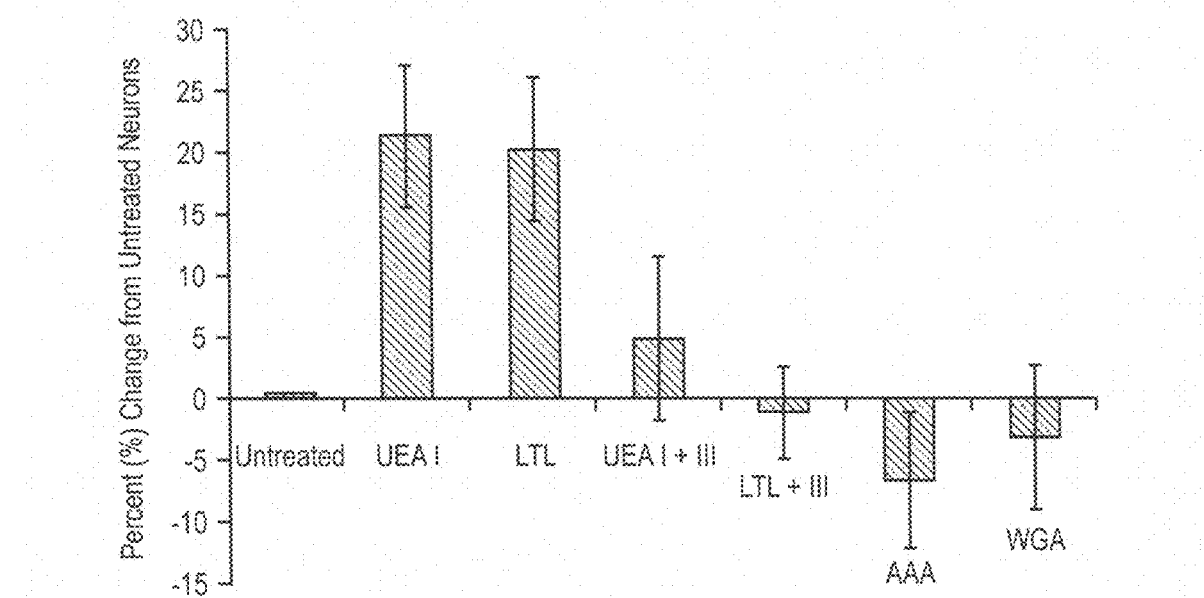

Hippocampal neurons were next treated with exogenous lectins to study their effect on neuronal growth, using quantitative methods as described in Example 3, supra. Cells were treated with UEA-I, LTL, UEA-I plus III, LTL plus III, AAA, or WGA (wheat germ agglutinin), or were untreated. FIG. 5B shows change in length of neurons as a percent of the untreated size. UEA-I and LTL stimulated growth by 21±6% and 20±6%, respectively, relative to the untreated control. As expected, competition with 400-fold excess III abolished the effects of UEA-I and LTL. Moreover, lectins selective for GlcNAc (WGA) and Fucα(1-3)Gal (AAA) failed to enhance neurite outgrowth, indicating that the growth-promoting activity is specific for Fucα(1-2)Gal carbohydrates.

Figure 6:
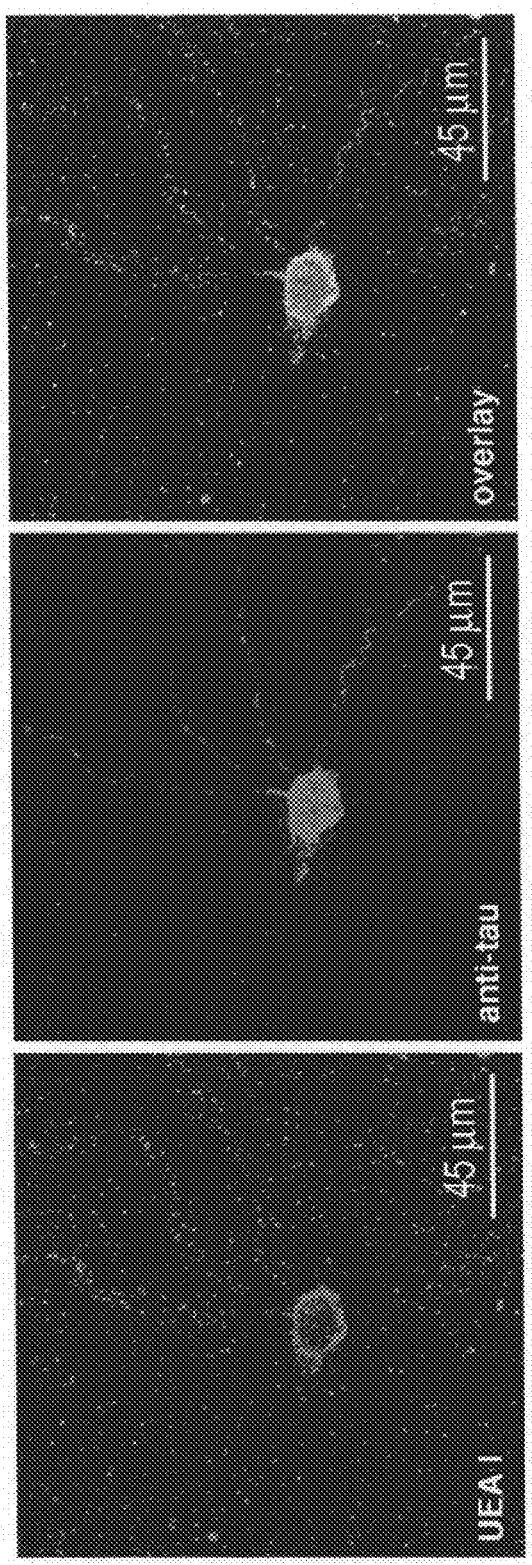
FIG. 6. Co-staining of E18 hippocampal neurons (23 days in vitro) with UEA-I lectin (1:100; green) and anti-tau antibody (1:600; red) in the presence of 10 μM PAO following lipid extraction. An overlay of both images is shown in yellow. Scale bars represent 45 μm.

FIG. 6 demonstrates that de-lipidation of the hippocampal cells did not disrupt binding of UEA-I. Box 1 shows UEA-I binding to the de-lipidated cells; in box 2 the binding is by anti-tau antibody; while in box 3 they are overlaid to show images very similar to those in FIG. 5A.

Example 5

Effects of 2-dGal on Neuronal Morphology

The effects of the amnesic compound 2-dGal (2-Deoxy-D-Galactose) were studied on neuronal morphology to determine its impact on the stimulation of neuronal growth by Fucα(1-2)Gal.

Figure 7:
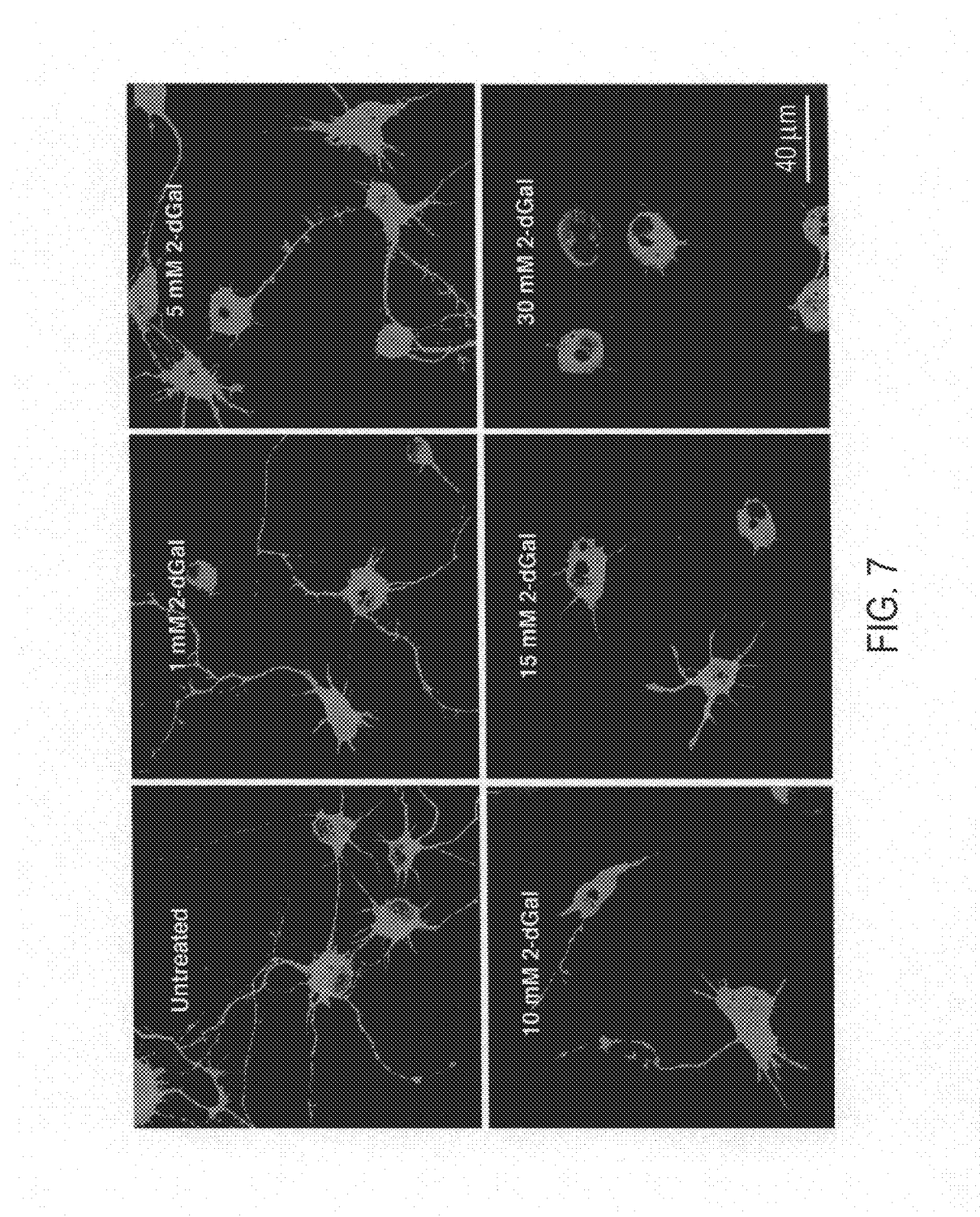
FIG. 7. Treatment of E18 hippocampal neurons with varying concentrations of 2-dGal. After 1 day in culture, neurons were treated with the specified concentrations of 2-dGal for 2 days, followed by immunostaining with anti-tau antibodies. Scale bar represents 40 μm.

Hippocampal neurons were plated on poly-DL-ornithine-coated glass coverslips as described above. After one day in culture, the medium was replaced with fresh medium, and the small molecules (2-dGal, 3-Deoxy-D-Galactose (3-dGal), or D-Galactose (Gal)) were added. A dose-response experiment was initially performed to determine the minimum concentration of 2-dGal needed to elicit an effect. Neurons were treated with varying concentrations of 2-dGal (1, 5, 10, 15, or 30 mM in 25 µL PBS with 475 µL of supplemented Neurobasal medium) for 2 days before immunostaining with anti-tau antibodies as described above. A gradual decrease in neurites can be seen (FIG. 7) as the concentration of 2-dGal increased. No cellular toxicity was observed at concentrations up to 30 mM 2-dGal, as demonstrated by trypan blue staining, adherence of the cells to the coverslip, and healthy cellular morphology. A concentration of 15 mM was used in subsequent experiments as it produced a strong effect on neurite outgrowth.

Figure 8A:
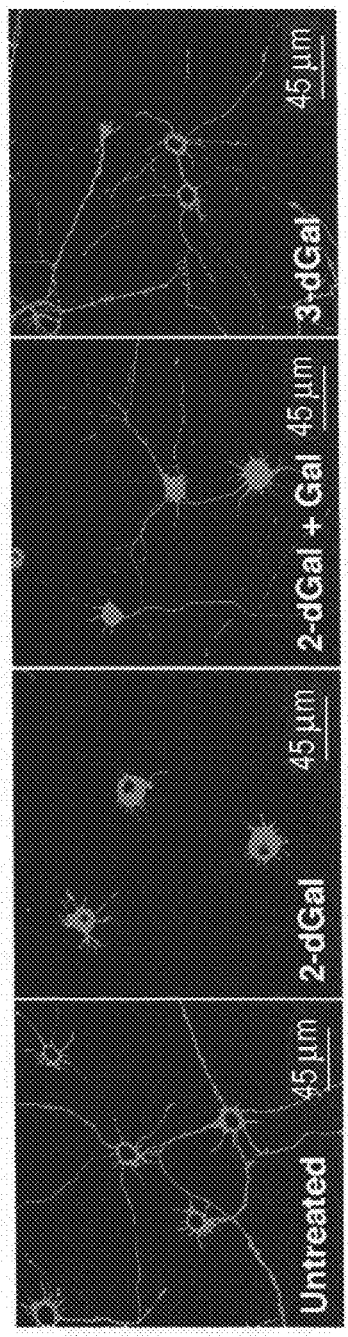
FIG. 8. (A) Treatment of neuronal cultures with 2-dGal diminishes expression of the Fucα(1-2)Gal epitope on glycoproteins. After a 4-day incubation with or without 30 mM 2-dGal, protein lysates were analyzed by Western blotting using an anti-Fucα(1-2)Gal antibody. Lane 1: Untreated neurons (75 μg total protein). Lane 2: Neurons treated with 30 mM 2-dGal (75 μg total protein). (B) Treatment of neurons with 2-dGal (15 mM), but not 3-dGal (15 mM), for 2 days inhibits neuronal growth. The effects of 2-dGal were rescued by subsequent treatment with Gal (75 mM) for an additional 2 days. Neurons were immunostained with an anti-tau antibody.

Cells were treated as above under 4 different conditions: (1) no treatment for 2 days, (2) incubation with 15 mM 2-dGal for 2 days, (3) incubation with 15 mM 2-dGal for 2 days followed by incubation with 75 mM Gal for 2 days, or (4)

incubation with 15 mM 3-dGal for 2 days. After adding the small molecules, cultures were incubated at 37° C., 5% $CO_2$, then washed once with PBS, and immunostained with anti-tau antibody as described above. FIG. 8A shows the immunostained cells, with untreated neurons, neurons treated with 2-dGal, neurons treated with 2-dGal and then rescued with Gal, and neurons treated with 3-dGal. Consistent with earlier studies (Jork, R., et al., *Neurosci. Res. Commun.* 5:105-110 (1989)), treatment of neurons with 2-dGal disrupted synthesis of the Fucα(1-2)Gal epitope on glycoproteins. The treated neurons also exhibited severely stunted neurites and failed to form synapses, as can be seen in box 2 of FIG. 5. The effects were fully reversible: subsequent addition of D-galactose led to regeneration of the neuronal processes, as can be seen in box 3. In contrast, 3-dGal had no impact on neurite outgrowth (compare box 4 with box 1). These results are consistent with a stimulatory role for Fucα(1-2)Gal glycoproteins and highlight the striking influence of Fucα(1-2)Gal carbohydrates on neuronal growth.

Figure 8B:
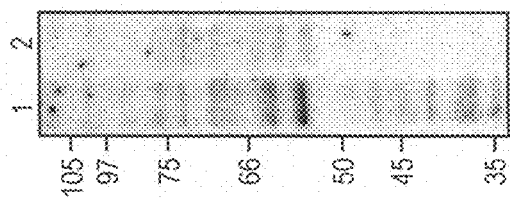

In addition to cells plated on coverslips, hippocampal neurons were grown in 30 mm dishes and treated with or without 30 mM 2-dGal (25 µL in PBS with 475 µL supplemented Neurobasal medium). After 4 days, cells were harvested with 2.5% trypsin, lysed with 1% boiling SDS with protease inhibitors, and cell lysates probed by Western blotting using the anti-Fucα(1-2)Gal antibody A46-B/B10 (Karsten, U., et al., *G. Br. J. Cancer,* 58:176-181 (1988)). Protein concentrations of the neuronal lysates were determined using the BCA Protein Assay (Pierce). Equal amounts of total protein were resolved by 10% SDS-PAGE, and proteins were transferred to PVDF membrane (Millipore) in 20 mM Tris-Cl pH 8.6/120 mM glycine/20% methanol. Western blots were blocked for 1 h with 3% periodated BSA (Glass, W. F., et al., *Anal. Biochem.,* 115:219-224 (1981)) and rinsed with TBST (50 mM Tris-Cl pH 7.4/150 mM NaCl/0.1% Tween-20). Blots were incubated with anti-Fucα(1-2)Gal antibody A46-B/B10 (0.5 µg/mL; gift from Dr. U. Karsten, Max-Delbruck Centre for Molecular Medicine, Berlin-Buch, Germany) in TBST overnight at 4° C. with constant rocking, then rinsed and washed twice for 10 min with TBST. Immunoreactivity was visualized by incubation with a horseradish peroxidase conjugated goat anti-mouse antibody (1:2500; Pierce) in TBST for 1 h followed by a rinse and four washes of 20 min with TBST. Blots were visualized by chemiluminescence using ECL reagents (Amersham) on X-Omat R film (Kodak). As can be seen in FIG. 8B, treated neurons exhibited significantly reduced levels of the Fucα(1-2)Gal epitope on several glycoproteins.

Example 6

Expression of Fucα(1-2)Gal on Glycoproteins is Enriched at the Neuronal Synapse

As Fucα(1-2)Gal sugars have been implicated in learning and memory formation, it was investigated whether Fucα(1-2)Gal glycoproteins are present in the hippocampus, a brain structure important for spatial learning and memory (Vermeer, H. J., et al., *Eur. J. Org. Chem.,* 2001:193-203 (2001)). Cell lysates from adult rat hippocampus, embryonic day 18 (E18) hippocampus, and cultured embryonic hippocampal neurons were analyzed by Western blotting using antibody A46-B/B 10, using methods described above. Antibody A46-B/B10 has been shown to induce amnesia in animals, suggesting that it recognizes one or more physiologically relevant epitopes.

Figure 9:
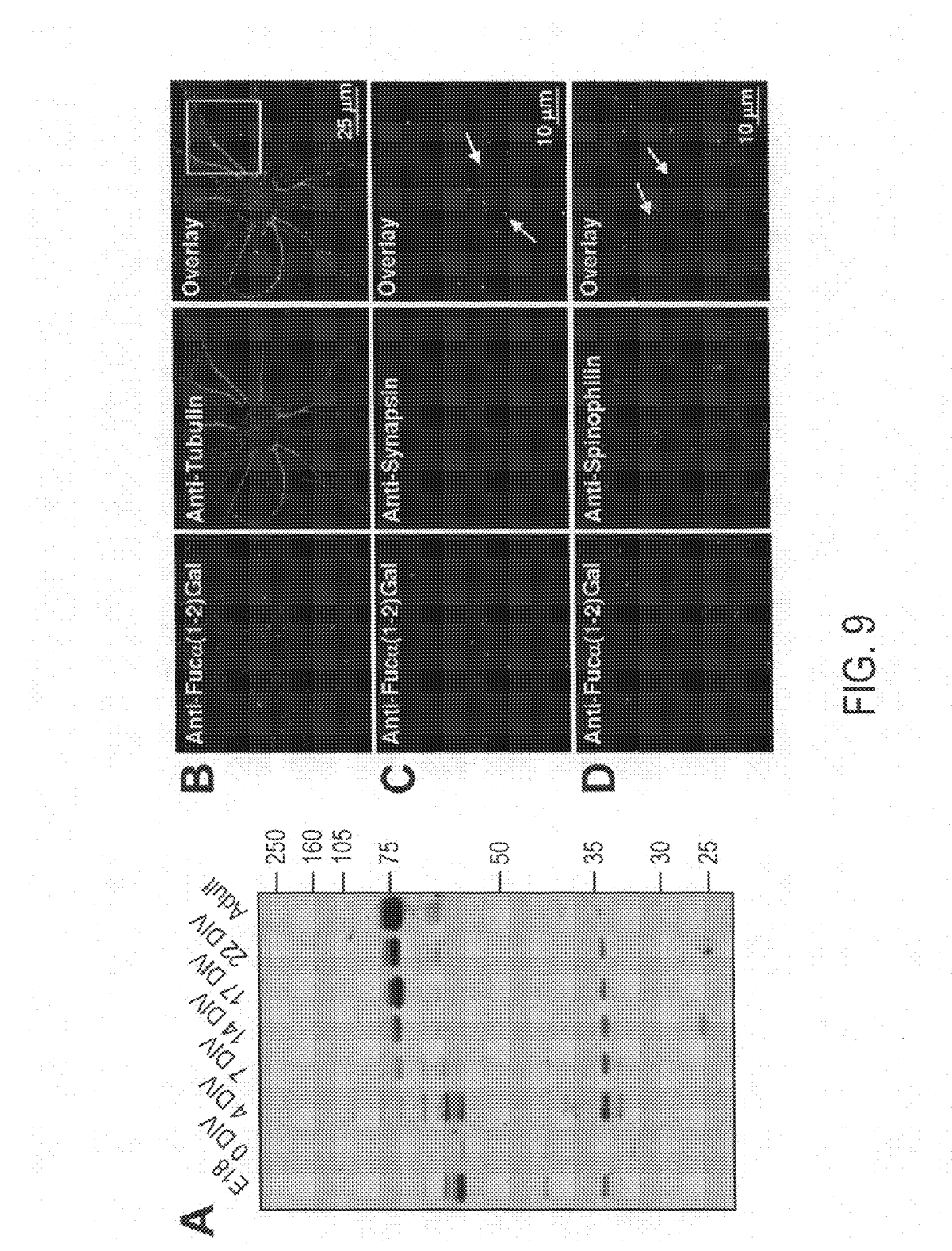
FIG. 9. Fucα(1-2)Gal is expressed on several glycoproteins in the hippocampus and is enriched in presynaptic nerve terminals. (A) Comparison of the glycoproteins present in E18 rat hippocampus, embryonic hippocampal neurons cultured for the indicated times, and adult rat hippocampus. Cellular lysates were resolved by SDS-PAGE and probed by Western blotting with antibody A46-B/B10. (B) Co-immunostaining of hippocampal neurons cultured for 14 DIV with antibody A46-B/B10 (green) and an antibody selective for the neuronal marker tubulin (red, panel B), the presynaptic marker synapsin (red, panel C), or the postsynaptic marker spinophilin (red, panel D). Images C and D are enlargements of the area indicated by the rectangle in B.

Fucα(1-2)Gal epitope is present on several distinct hippocampal proteins during neuronal development (FIG. 9A). Three major glycoproteins of approximately 35, 60, and 65 kDa are prominently observed in E18 embryonic tissue, yet their expression is significantly reduced in the adult hippocampus. In contrast, glycoproteins of approximately 73 and 75 kDa are found in mature neuronal cultures and in adult brain tissue. Expression of Fucα(1-2)Gal is observed on multiple proteins in neurons cultured for 4 and 7 days in vitro, periods when axons, dendrites and functional synapses are being formed. These results indicate that the Fucα(1-2)Gal modification is present on two major proteins in the adult hippocampus and several distinct proteins in developing neurons, suggesting that expression and/or fucosylation of these proteins changes dramatically during the course of neuronal development.

It was also found that Fucα(1-2)Gal is enriched at synapses. The subcellular localization of Fucα(1-2)Gal sugars in neurons was determined by fluorescent staining. Hippocampal neurons were cultured for 14 DIV to allow for synapse formation and then fixed, permeabilized and co-immunostained with antibody A46-B/B10 and an antibody against the neuronal marker tubulin, using methods described above. The Fucα(1-2)Gal epitope exhibited a punctate pattern consistent with enriched localization to neuronal synapses (FIG. 9B). To examine whether the sugar was present at pre- or postsynaptic terminals, neurons were co-stained for Fucα(1-2)Gal (A46-B/B10 antibodies) and the presynaptic marker synapsin I (anti-synapsin antibodies; 1:5000; Molecular Probes) or the postsynaptic marker spinophilin (anti-spinophilin antibodies; 1:10000; gift of Paul Greengard and Patrick Allen, described in *PNAS,* 94:9956-61 (1997).) in 3% BSA for 2 h at 37° C.

Fucα(1-2)Gal labeling was observed in a subpopulation of the synapses (58±2%; n=350), overlapping with synapsin-positive puncta (yellow dots, FIG. 9C) and generally apposing spinophilin-positive puncta (green dots next to red dots, FIG. 9D). Membrane de-lipidation using MeOH/$CHCl_3$ (described above) did not alter the immunostaining pattern, which confirms the staining of glycoproteins rather than glycolipids. These findings indicate that Fucα(1-2)Gal sugars are enriched on glycoproteins in presynaptic nerve terminals.

Example 7

Synapsin IA and IB are the Major Fucα(1-2)Gal Glycoproteins in the Hippocampus

The identity of neuronal glycoproteins modified by the Fucα(1-2)Gal epitope was studied. Attempts to purify Fucα(1-2)Gal glycoproteins from brain extracts using antibody A46-B/B10 were unsuccessful due to the relatively weak binding affinity of the antibody for the carbohydrate epitope. Fucose-specific lectins such as LTL and UEA-I also displayed weak affinity and broad specificity, resulting in limited enrichment of Fucα(1-2)Gal glycoproteins. To circumvent these challenges, potential glycoproteins were identified using a combination of subcellular fractionation, gel electrophoresis, and matrix-assisted laser desorption/ionization time-of-flight mass spectrometry (MALDI-TOF MS).

Adult male Sprague-Dawley rat (100-150 g) hippocampi were homogenized in 50 mM Tris-HCl pH 8.0, 150 mM NaCl, 0.2% sodium deoxycholate, 1% NP-40 supplemented with protease inhibitors with a glass Dounce homogenizer and sonicated briefly. Supernatants were clarified by centrifugation at 12,000×g for 10 min, and protein concentrations were determined using the BCA protein assay method (Pierce). Lysates were enriched in synaptic proteins using standard subcellular fractionation procedures. The crude synaptosomal fractions were resolved by 1-D or 2-D gel electrophoresis and analyzed by Western blotting with antibody A46-B/B10 or stained with Coomassie Brilliant Blue. As observed previously, two major glycoproteins of approximately 73 and 75 kDa were recognized by antibody A46-B/B10.

Proteins of interest were identified by immunoblotting and excised from the corresponding Coomassie-stained gel, digested with trypsin, and identified by MALDI-TOF MS. MS analysis revealed three potential Fucα(1-2)Gal-containing glycoproteins: synapsin Ia, synapsin Ib, and N-ethylmaleimide-sensitive factor (NSF). Eleven measured peptides matched the masses calculated from the National Center for Biotechnology Information (NCBI) non-redundant database for both synapsins Ia and Ib with greater than 50 ppm accuracy, and the unmodified matching peptides covered 11.2% of the amino acid sequence (Table 1). For NSF, 24 matching peptides were detected within 50 ppm, which provided 29.7% overall sequence coverage (Table 2).

TABLE 1

SUMMARY OF PEPTIDE MASSES IDENTIFED BY MALD1-MS THAT MATCHED PEPTIDES CORRESPONDING TO SYNAPSIN I

| Amino Acid | | | Peptide | | Experimental | Delta |
|---|---|---|---|---|---|---|
| Start | End | Mass | Sequence | Modifications | Mass | ppm |
| 1 | 5 | 696.3503 | (—) MNYLR | | 696.39 | 57 |
| 414 | 420 | 816.4402 | (K) MTQALPR | | 816.4414 | 1.5 |
| 414 | 420 | 832.4351 | (K) MTQALPR | Met-Ox | 832.4321 | −3.6 |
| 1 | 6 | 852.4514 | (—) MNYLRR | | 852.4528 | 1.6 |
| 1 | 6 | 868.4463 | (—) MNYLRR | Met-Ox | 868.4684 | 25 |
| 329 | 336 | 878.4372 | (R) TSVSGNWK | | 878.4353 | −2.2 |
| 555 | 563 | 908.459 | (R) QAGPPQATR | PYroGlu | 908.47 | 12 |
| 135 | 142 | 924.5155 | (K) IHGEIDIK | | 924.4762 | −42 |
| 555 | 563 | 925.4856 | (R) QAGPPQATR | | 925.4714 | −15 |
| 187 | 194 | 930.4256 | (R) QHAFSMAR | PyroGlu | 939.4778 | 56 |
| 187 | 194 | 946.4205 | (R) OHAFSMAR | PyroGlu, Met-Ox | 946.4745 | 57 |
| 187 | 194 | 947.4521 | (R) QHAFSMAR | | 947.4592 | 7.4 |
| 601 | 610 | 951.4648 | (R) QASQAGPGPR | PyroGlu | 951.4512 | −14 |
| 187 | 194 | 963.4471 | (R) QHAFSMAR | Met-Ox | 963.4368 | 11 |
| 270 | 279 | 1012.4457 | (K) MGHAHSGMGK | | 1012.4116 | −34 |
| 564 | 574 | 1035.5475 | (R) QASISGPAPPK | PyroGlu | 1035.5238 | −23 |
| 575 | 585 | 1041.5234 | (K) VSGASPGGQQR | | 1041.5512 | 27 |
| 564 | 574 | 1052.574 | (R) QASISGPAPPK | | 1052.5302 | −42 |
| 134 | 142 | 1052.6104 | (K) KIHGEIDIK | | 1052.5302 | −76 |
| 404 | 413 | 1137.6883 | (K) QLIVELVVNK | PyroGlu | 1137.5359 | −134 |
| 177 | 186 | 1187.7152 | (R) SLKPDFVLIR | | 1187.6866 | −24 |
| 270 | 281 | 1239.6091 | (K) MGHAHSGMGKVK | | 1239.576 | −27 |
| 300 | 311 | 1326.6582 | (K) TYATAEPFIDAK | | 1326.6083 | −38 |
| 257 | 269 | 1453.7612 | (K) EMLSSTTYPVVVK | | 1453.6399 | −83 |
| 586 | 600 | 1479.8072 | (R) QGPPQKPPGPAGPIR | PyroGlu | 1479.7356 | −48 |
| 586 | 600 | 1496.8338 | (R) QGPPQKPPGPAGPIR | | 1496.7674 | −44 |
| 187 | 199 | 1552.7079 | (R) QHAFSMARNGDYR | | 1552.7255 | 11 |
| 429 | 444 | 1561.8087 | (R) GSHSQTPSPGALPLGR | | 1561.7179 | −58 |
| 316 | 328 | 1598.8477 | (R) VQKIGQNYKAYMR | | 1598.801 | −29 |
| 115 | 128 | 1635.8746 | (R) VLLVIDEPHTDWAK | | 1635.7801 | −58 |
| 337 | 352 | 1756.7846 | (K) TNTGSAMLEQIAMSDR | 2Met-Ox | 1756.6918 | −53 |
| 282 | 299 | 2000.0089 | (K) VDNQHDFQDIASVVALTK | | 1999.8509 | −79 |
| 86 | 108 | 2034.9481 | (K) QTTAAAAATFSEQVGGGSGGAGR | PyroGlu | 2034.9021 | −23 |
| 86 | 108 | 2051.9746 | (K) QTTAAAAATFSEQVGGGSGGAGR | | 2051.8296 | −71 |
| 238 | 256 | 2277.1556 | (K) KLGTEEFPLIDQTFYPNHK | | 2276.9218 | −103 |
| 445 | 474 | 3038.5309 | (R) QTSQQPAGPPAQQRPPPQGGPPQPGPGPQR | | 3038.1725 | −118 |

Peptides in bold were matched with <50 ppm. Ion signals produced from trypsin auto-digestion peptides were used as an internal mass calibration standard. Proteins were identified with Protein Prospector to query the list of tryptic peptide masses for known proteins using the non-redundant sequence database maintained by the NCBI.

TABLE 2

SUMMARY OF PEPTIDE MASSES IDENTIFIED BY MALDI-MS THAT MATCHED PEPTIDES CORRESPONDING TO NSF

| Amino Acid | | | Peptide | | Experimental | Delta |
|---|---|---|---|---|---|---|
| Start | End | Mass | Sequence | Modifications | Mass | ppm |
| 267 | 271 | 573.3724 | (K) TLLAR | | 573.3803 | 14 |
| 703 | 708 | 715.4507 | (K) VWIGIK | | 715.4384 | −17 |
| 510 | 516 | 830.4161 | (K) WGDPVTR | | 830.4092 | −8.3 |
| 226 | 232 | 913.442 | (K) EFSDIFR | | 913.4365 | −5.9 |
| 640 | 648 | 973.6046 | (K) LLIIGTTSR | | 973.578 | −27 |
| 573 | 581 | 983.4872 | (K) MIGFSETAK | | 983.5007 | 14 |
| 573 | 581 | 999.4821 | (K) MIGFSETAK | Met-Ox | 999.483 | 0.67 |

TABLE 2-continued

SUMMARY OF PEPTIDE MASSES IDENTIFIED BY MALDI-MS THAT MATCHED PEPTIDES CORRESPONDING TO NSF

| Amino Acid | | | Peptide | | Experimental | Delta |
|---|---|---|---|---|---|---|
| Start | End | Mass | Sequence | Modifications | Mass | ppm |
| 587 | 594 | 999.5151 | (K) KIFDDAYK | | 999.483 | −32 |
| 272 | 280 | 1013.5566 | (R) QIGKMLNAR | PyroGlu | 1013.4748 | −81 |
| 284 | 293 | 1082.621 | (K) VVNGPEILNK | | 1082.5456 | −70 |
| 540 | 649 | 1101.6996 | (R) KLLIIGTTSR | | 1101.6044 | −86 |
| 294 | 303 | 1137.554 | (K) YVGESEANIR | | 1137.5359 | −16 |
| 808 | 617 | 1142.6574 | (R) LLDWPIGPR | | 1142.6256 | 28 |
| 404 | 413 | 1201.717 | (R) LQILHIHTAR | | 1201.6662 | −42 |
| 692 | 702 | 1201.7268 | (R) TTIAQQVKGKK | | 1201.6662 | −50 |
| 305 | 314 | 1207.5595 | (K) LFADAEEEQR | | 1207.531 | −24 |
| 151 | 161 | 1247.6193 | (K) DIESMOPSILK | | 1247.5715 | −38 |
| 435 | 446 | 1291.6646 | (K) NSFGAELEGLVR | | 1291.6322 | −25 |
| 556 | 566 | 1294.6683 | (K) IAEESNFPFIK | | 1294.6234 | −35 |
| 304 | 314 | 1335.6545 | (R) KLFADAEEEQR | | 1335.5976 | −43 |
| 105 | 116 | 1383.6028 | (K) KSNDSNPYDTDK | | 1383.6362 | 24 |
| 272 | 283 | 1383.7418 | (R) QIGKMLNAREPK | PyroGlu, Met-Ox | 1383.6362 | −76 |
| 218 | 232 | 1700.8318 | (K) MGIGGLDKEFSDIFR | Met-Ox | 1700.7015 | −77 |

Peptides in bold were matched with <50 ppm. Ion signals produced from trypsin auto-digestion peptides were used as an internal mass calibration standard. Proteins were identified with Protein Prospector to query the list of tryptic peptide masses for known proteins using the non-redundant sequence database maintained by the NCBI.

Figure 10:
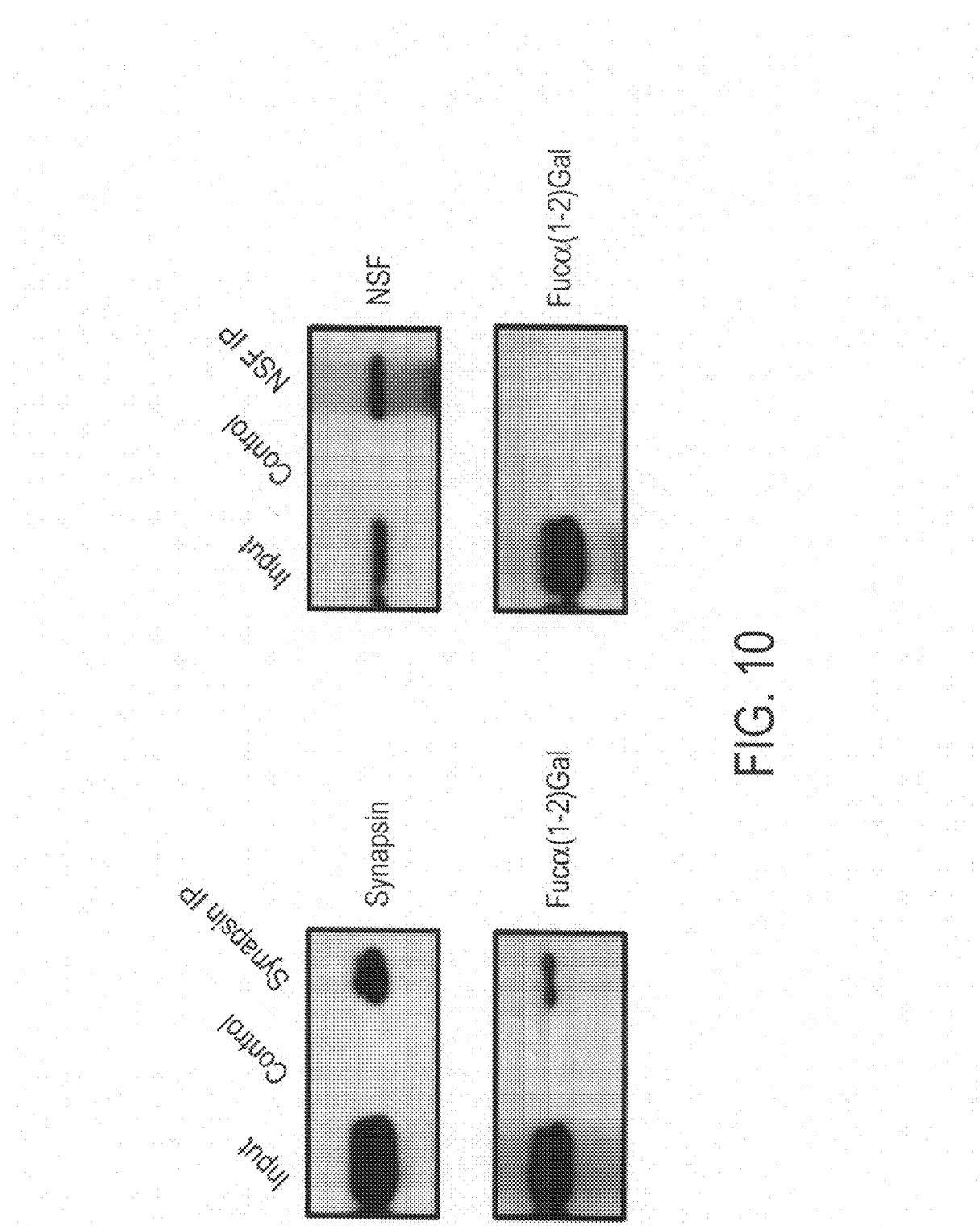
FIG. 10. Synapsin Ia and Ib are Fucα(1-2)Gal glycoproteins. Immunoprecipitated synapsin I but not NSF is detected by antibody A46-B/B10. Input, lysate used for immunoprecipitation; Control, immunoprecipitation in the absence of antibody; Synapsin or NSF IP, immunoprecipitated synapsin or NSF. The top two panels were immunoblotted with an anti-synapsin (Left) or anti-NSF (Right) antibody, and the bottom two panels were probed with antibody A46-B/B10. Synapsin Ia appeared in darker exposures of the blot (data not shown).

To establish whether synapsin Ia/Ib and NSF were indeed recognized by antibody A46-B/B10, each protein was immunoprecipitated (approximately 2 mg/mL lysate using an anti-synapsin (Chemicon) or anti-NSF (Synaptic Systems) antibody), and examined by Western blotting with antibody A46-B/B10 using procedures described above. Upon immunoprecipitation, synapsin Ia and Ib were specifically detected by the antibody, whereas NSF was not recognized (FIG. 10). Treatment of the synapsins with PNGaseF and EndoH, enzymes that cleave N-linked oligosaccharides from proteins, did not abolish the interaction with antibody A46-B/B10, suggesting that the Fucα(1-2)Gal moiety is present on an O-linked glycan (data not shown). Thus, synapsin Ia and Ib are the two major hippocampal glycoproteins recognized by antibody A46-B/B10, and they likely contain an O-linked oligosaccharide.

Example 8

Characterization of the Carbohydrate Structure on Synapsin

To gain insight into the structural determinants recognized by antibody A46-B/B10, competition enzyme-linked immunosorbent assay (ELISA) experiments were performed using a series of fucose analogs (FIG. 12 A, B). Purified bovine synapsin Ia/Ib (Ueda, T., et al., *J. Biol. Chem.*, 252:5155-5163 (1977)) was a supplied by Drs. P. Greengard and A. Nairn (The Rockefeller University, New York, N.Y.). The protein was immobilized on a microtiter plate by incubation in 50 mM NaHCO$_3$, pH 9.0 at 4° C. overnight. Antibody A46-B/B10 (0.02 mg/mL) and the competitors (0.078-5 mM) were incubated in TBST (50 mM Tris-HCl pH 7.4, 150 mM NaCl, 0.1% Tween-20) at 4° C. overnight and then transferred to the microtiter plate. The wells were washed with TBST and incubated with a goat anti-mouse secondary antibody conjugated to alkaline phosphatase (1:500) at rt for 1 h. The wells were washed with TBST and developed with p-nitrophenyl phosphate. Inhibition curves were generated using PRISM (GraphPAD Software, Inc.).

The monosaccharide competitors, ethyl α/β-L-fucopyranoside (L-Fuc-α-OEt and L-Fuc-β-OEt) and ethyl α/β-D-fucopyranoside (D-Fuc-α-OEt and D-Fuc-β-OEt), were synthesized from L- or D-fucose using a modified Fischer glycosylation reaction (Vermeer, H. J., et al., supra).

Figure 11:
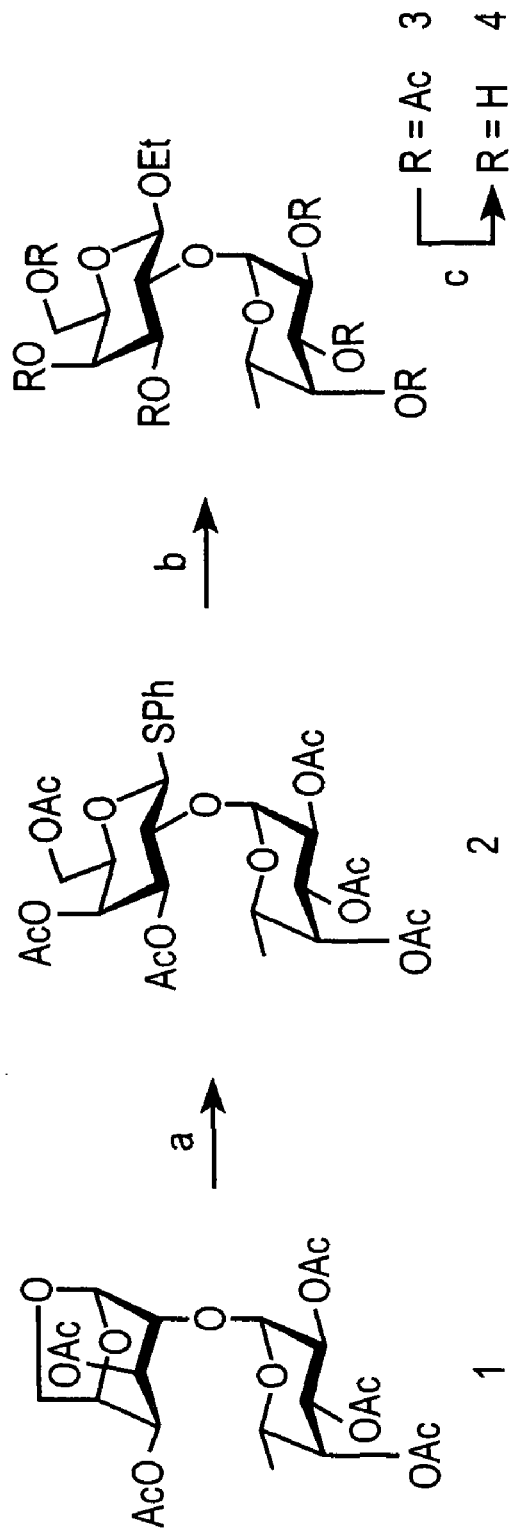
FIG. 11. Synthesis of Fucα(1-2)Gal-β-OEt (4). Conditions: (a) i. TMSSPh, ZnI$_2$, CH$_2$Cl$_2$; ii. TBAF, THF (76%, two steps); iii. Ac$_2$O, pyr. (quant.). (b) NIS, AgOTf, EtOH, CH$_2$Cl$_2$ (68%). (c) NaOMe, MeOH (quant.).

Disaccharide Fucα(1-2)Gal-β-OEt was synthesized from the known O-(2,3,4-tri-O-benzyl-α-L-fucopyranosyl) trichloroacetimidate. (FIG. 11).

3,4,6-Tri-O-(2,3,4-tri-O-acetyl-α-L-fucopyranosyl)-1-phenylthio-β-D-galactopyranoside (2): 3,4-Di-O-acetyl-1,6-anhydro-2-O-(2,3,4-tri-O-acetyl-α-L-fucopyranosyl)-β-D-galactopyranose (Wegmann, B., et al., supra) (FIG. 11, Compound 1, 1.8 g, 3.40 mmol), (phenylthio)trimethylsilane (2.0 mL, 10.4 mmol) and zinc iodide (3.30 g, 10.4 mmol) were stirred in CH$_2$Cl$_2$ (20 mL) for 21 h. The mixture was diluted with EtOAc (120 mL) and washed successively with saturated aqueous NaHCO$_3$ (150 mL), water (3×50 mL) and brine (20 mL). The organic layer was then dried over Na$_2$SO$_4$, filtered, and concentrated in vacuo. The residue was dissolved in dry THF (15 mL) and 1 M tetrabutylammonium fluoride in THF (6.0 mL) was added. After stirring 20 min, the solvent was removed in vacuo. The residue was dissolved in EtOAc (60 mL), washed with water (3×30 mL), saturated aqueous NaHCO$_3$ (30 mL), and brine (30 mL), dried over Na$_2$SO$_4$, filtered, and concentrated to afford the crude β-thioglycoside (1.60 g, 76%). To a solution of the α-thioglycoside (310 mg, 0.50 mmol) in pyridine (6.0 mL) was added acetic anhydride (3.0 mL). After stirring for 12 h, the solvent was removed in vacuo, and residual pyridine was removed by azeotroping with toluene. The product was purified by flash chromatography (3:1 hexanes/EtOAc) to afford 2 as a white solid (quant.). $^1$H NMR (300 MHz, CDCl$_3$): 7.59-7.20 (m, 5H), 5.83 (dd, 1H, J=3.4, 11.0 Hz), 5.74 (d, 1H, J=3.8 Hz), 5.60 (dd, 1H, J=1.1, 3.4 Hz), 5.44 (dd, 1H, J=3.8, 11.0 Hz), 5.42 (dd, 1H, J=0.8, 3.5 Hz), 5.19 (dd, 1H, J=3.5, 10 Hz), 4.62 (m, 1H), 4.13 (dd, 1H, J=7.0, 10.2 Hz), 4.12 (dd, 1H, J=7.7, 10 Hz), 4.06 (dd, 1H, J=7.3, 10.2 Hz), 3.83 (dd, 1H, J=7.7 Hz), 3.41 (ddd, 1H, J=0.8, 7.0, 7.3 Hz), 1.93 (s, 3H), 1.87 (s, 3H), 1.76 (s, 3H), 1.66 (2s, 6H), 1.51 (s, 3H), 1.12 (d, 3H, J=6.5 Hz). $^{13}$C NMR (75 MHz, CDCl$_3$): 170.6, 170.5, 170.2, 170.0, 169.9, 133.2, 131.7, 129.3, 127.7, 100.2, 98.2, 87.8, 73.1, 71.0, 70.1, 68.1, 67.9, 67.3, 65.8, 61.8, 20.8, 20.7, 15.9. HRMS m/z Calculated for $C_{30}H_{38}O_{15}SNa$ [M+Na]$^+$ 693.1253. Found 693.1271.

Ethyl 3,4,6-tri-O-(2,3,4-tri-O-acetyl-α-L-fucopyranosyl)-1-β-D-galactopyranoside (3): Compound 2 (140 mg, 0.20 mmol) was co-evaporated with toluene and dissolved in $CH_2Cl_2$ (1.5 mL) and EtOH (10 mL, 0.20 mmol) containing 4 Å molecular sieves. After stirring for 10 min, the mixture was cooled to −20° C. N-Iodosuccinimide (59 mg, 0.20 mmol) followed by silver triflate (61 mg, 0.20 mmol) was added. The reaction was then allowed to warm to rt over 2 h. After dilution with $CH_2Cl_2$, the reaction was filtered, and the filtrate was washed with saturated aqueous $Na_2SO_4$, filtered, and concentrated. The product was purified by flash chromatography (3:1 hexanes/EtOAc) to afford 3 as a white solid (68%, α:β=1:3): only the β-isomer was used. $^1$H NMR (300 MHz, $CDCl_3$): 5.83 (dd, 1H, J=1.1 Hz), 5.74 (d, 1H, J=3.8 Hz), 5.60 (dd, 1H, J=3.4 Hz), 5.33 (dd, 2H, J=3.6, 8.4 Hz), 5.27 (m, 2H), 5.00 (dd, 1H, J=3.3, 9.9 Hz), 4.98 (dd, 1H, J=4.5, 10.2 Hz), 4.08 (dd, 1H, J=6.6, 11.7 Hz), 4.00 (dd, 1H, J=6.9, 9.3 Hz), 3.92 (dd, 1H, J=7.8, 9.9 Hz), 3.85 (ddd, 1H, J=1.0 Hz), 3.59 (m, 4H), 2.13 (s, 6H), 2.11 (s, 3H), 2.02 (s, 3H), 1.98 (s, 3H), 1.96 (s, 3H), 1.12 (d, 3H, J=6.6 Hz). $^{13}$C NMR (75 MHz, $CDCl_3$): 170.8, 170.7, 170.1, 169.9, 169.3, 168.8, 100.6, 97.3, 72.3, 71.2, 68.6, 68.4, 68.2, 67.8, 65.4, 64.7, 21.2, 21.1, 21.0, 16.3. HRMS m/z Calculated for $C_{26}H_{39}O_{16}$ [M+H]$^+$ 607.2238. Found 607.2231.

Ethyl O-(α-L-fucopyranosyl)-(1-2)-β-D-galactopyranoside (4): A solution of 3 (90 mg, 0.15 mmol) and NaOMe (0.20 mL, 0.5 M in MeOH) in MeOH (2.0 mL) was stirred for 12 h. The solution was neutralized with Amberlite IR-120 (H$^+$ form) ion exchange resin, filtered, and concentrated to afford 4 as a white foam (quant.). $^1$H NMR (300 MHz, $D_2O$): 5.13 (d, 1H, J=3.8 Hz), 4.42 (d, 1H, J=7.8 Hz), 4.27-4.25 (m, 1H), 4.02-3.93 (m, 1H), 3.90-3.87 (m, 1H), 3.83 (m, 1H), 3.82 (m, 1H), 3.81-3.80 (m, 2H), 3.77-3.76 (m, 1H), 3.70-3.69 (m, 1H), 3.61-3.59 (m, 5H), 3.55-3.54 (m, 1H), 1.40-1.22 (m, 3H). $^{13}$C NMR (75 MHz, $D_2O$): 103.4, 100.7, 78.9, 75.5, 73.9, 72.5, 70.3, 69.4, 69.1, 67.5, 61.6, 57.7, 15.8. HRMS m/z Calculated for $C_{14}H_{26}O_{10}$ [M+Na]$^+$ 377.1423. Found 377.1428.

Figure 12A:
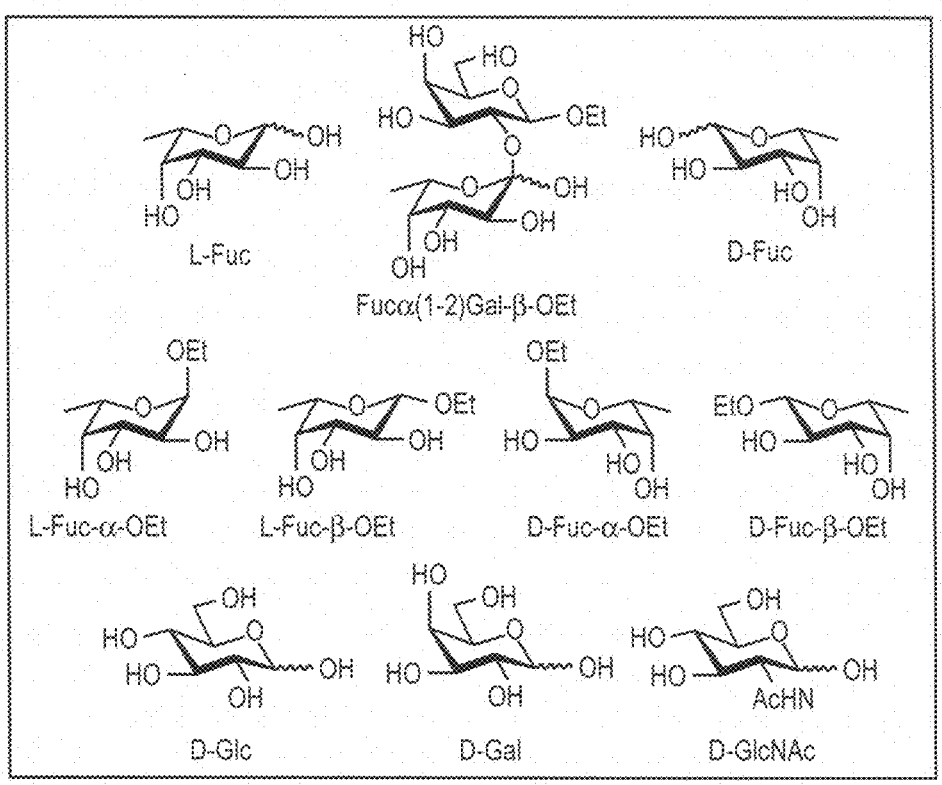
FIG. 12. (A) Structures of the mono- and disaccharide competitors used in this study. (B) Competition ELISA shows that binding of antibody A46-B/B10 to bovine synapsin I is selectively inhibited by monosaccharides containing L-fucose and the disaccharide Fucα(1-2)Gal.
Figure 12B:
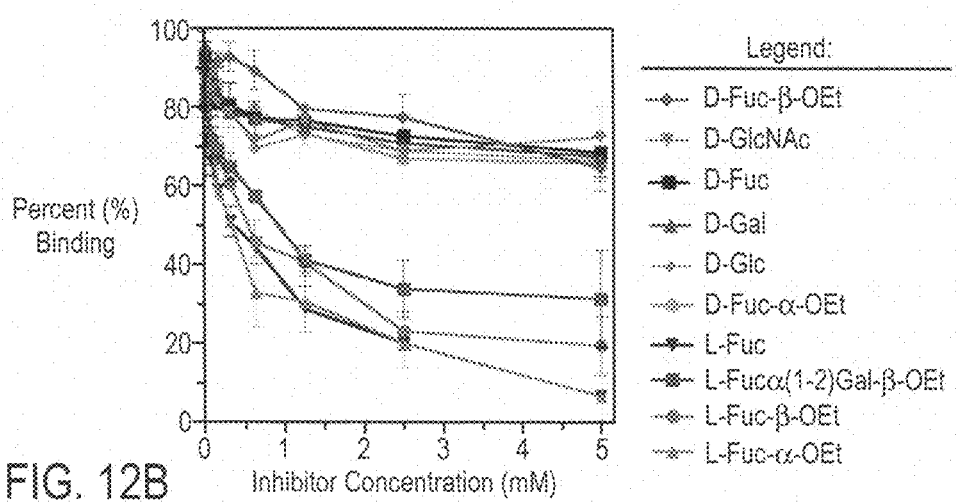

Synapsin Ia and Ib from bovine brain were immobilized on a microtiter plate, and binding of antibody A46-B/B10 to synapsin was assessed in the presence of varying concentrations of the competitors (see FIG. 12A for structures of the competitor molecules). Whereas L-fucose, L-Fuc-α-OEt, and L-Fuc-β-OEt were effective at inhibiting antibody binding to synapsin Ia and Ib, the corresponding D-fucose sugars showed poor inhibition (see FIG. 12B, which compares % binding vs. inhibitor concentration in mM of the competitors). Furthermore, other naturally occurring sugars, including D-glucose (D-Glc), D-galactose (D-Gal), and N-acetyl-D-glucosamine (D-GlcNAc) did not compete with synapsin for antibody binding. The IC$_{50}$ values of L-fucose, L-Fuc-α-OEt, and L-Fuc-β-OEt were comparable to that of the disaccharide Fucα(1-2)Gal-β-OEt, consistent with the specificity observed for some fucose-binding lectins such as AAA. (Haselhorst, T., et al., *J. Am. Chem. Soc.*, 123:10705-10714 (2001))

Figure 13:
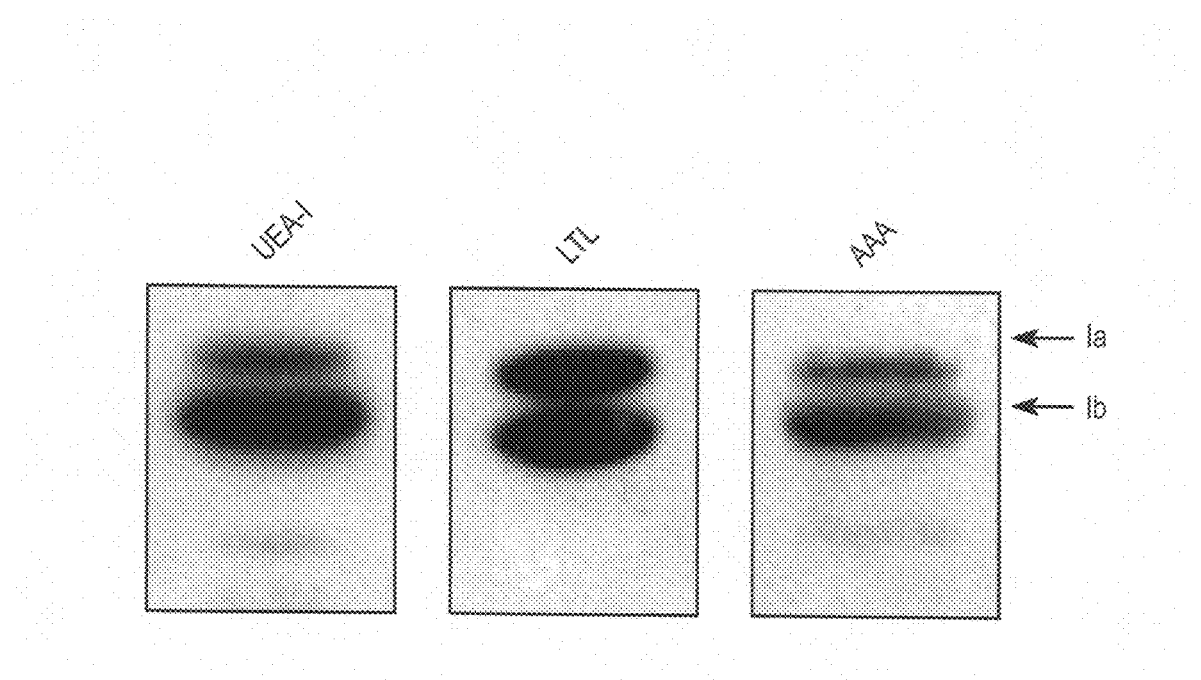
FIG. 13. Synapsin is recognized by L-fucose-specific lectins. Purified bovine synapsin I was resolved by SDS-PAGE and analyzed by immunoblotting with the indicated lectins conjugated to horseradish peroxidase.

Fucose-specific lectins and glycosidases were employed to gain further insight into the glycan structure on synapsin. Using methods described above, three lectins were compared for their ability to bind the synapsins: LTL, UEA-I, and AAA. Whereas LTL and UEA-I lectins interact strongly with terminal Fucα(1-2)Gal carbohydrates, AAA has been reported to bind the disaccharide only weakly (Alonso, E., et al., supra). Both LTL and UEA-I readily detected synapsin Ia and Ib, consistent with the presence of a Fucα(1-2)Gal moiety on synapsin (FIG. 13). However, AAA lectin was also capable of recognizing the epitope on synapsin, indicating that fucose-specific lectins alone cannot be used to distinguish the precise fucose-galactose linkage on synapsin.

As fucosidases have been shown to hydrolyze specific glycosidic linkages, synapsin Ia and Ib were treated with an α-(1-2)-fucosidase or an α-(1-3,4)-fucosidase from *Xanthomonas manihotis*. Purified bovine synapsin Ia/b (100 ng) was denatured in boiling 1% SDS for 1 min and neutralized by an equivalent volume of NETFD buffer (50 mM Tris-HCl pH 7.4, 100 mM NaCl, 5 mM EDTA, 50 mM NaF, 6% NP-40 supplemented with protease inhibitors). Reactions were performed in 50 μL fractions using one of the fucosidases (400 μU/100 ng synapsin; Calbiochem) in 50 mM sodium acetate buffer at pH 5.0 at 37° C. Samples were resolved by SDS-PAGE and analyzed by immunoblotting and densitometry with NIH Image 1.62 software. Statistical analysis was performed using StatView (SAS Institute Inc.).

Figures 14A, 14B:
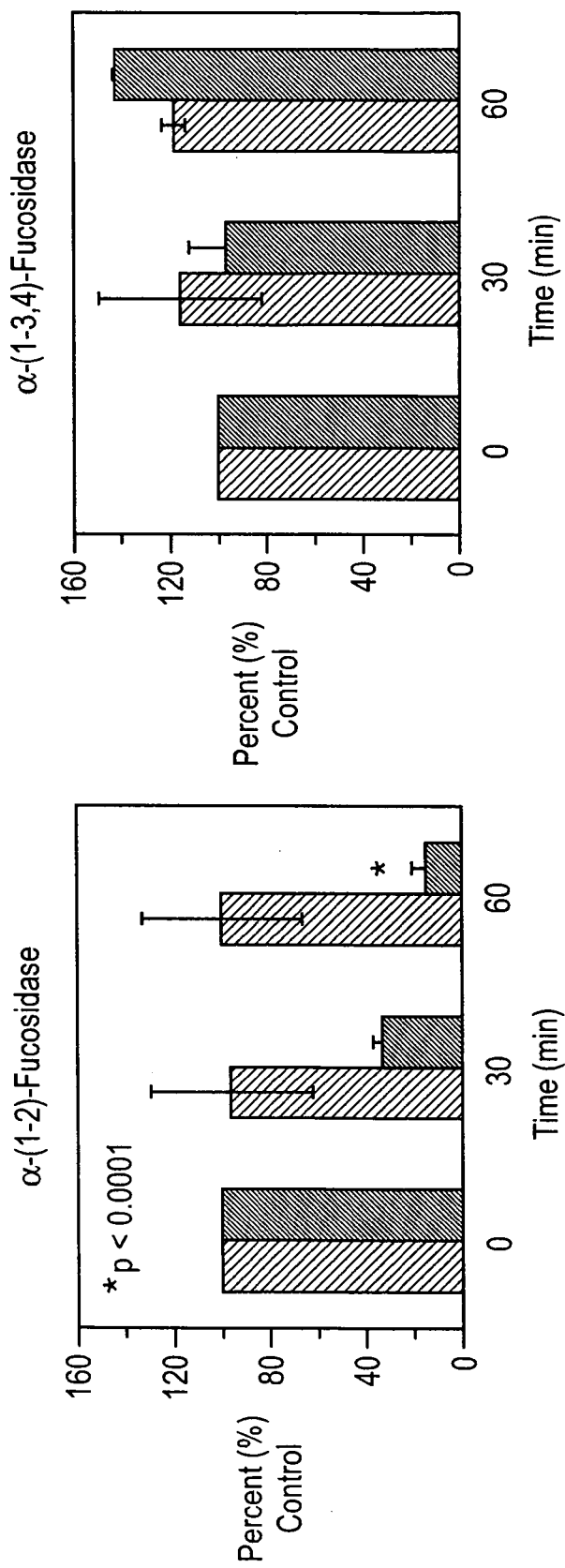
FIG. 14. Treatment of bovine synapsin I with α-(1-2)-fucosidase significantly reduces the fucosylation of synapsin, as demonstrated by Western blotting with antibody A46-B/B10 (FIG. 14A). In contrast, α-(1-3,4)-fucosidase had no effect on synapsin fucosylation (FIG. 14B). Left-hand bars indicate synapsin protein levels and right-hand bars indicate synapsin fucosylation levels after treatment with the fucosidase for the indicated times.

After treatment, the fucosylation and protein levels of synapsin were measured by immunoblotting. Rapid deglycosylation of synapsin was observed upon treatment with the α-(1-2)-fucosidase (FIG. 14A). In contrast, the α-(1-3,4)-fucosidase, which hydrolyzes both Fucα(1-3) and Fucα(1-4) linkages, had no effect on the fucosylation levels of synapsin, even after 6 h of treatment (FIG. 14B and data not shown). Together, these results provide strong evidence that synapsin Ia and Ib contain the critical Fucα(1-2)Gal epitope.

Example 9

Subcellular Distribution of Fucosylated Synapsin is Extensive

Figure 15:
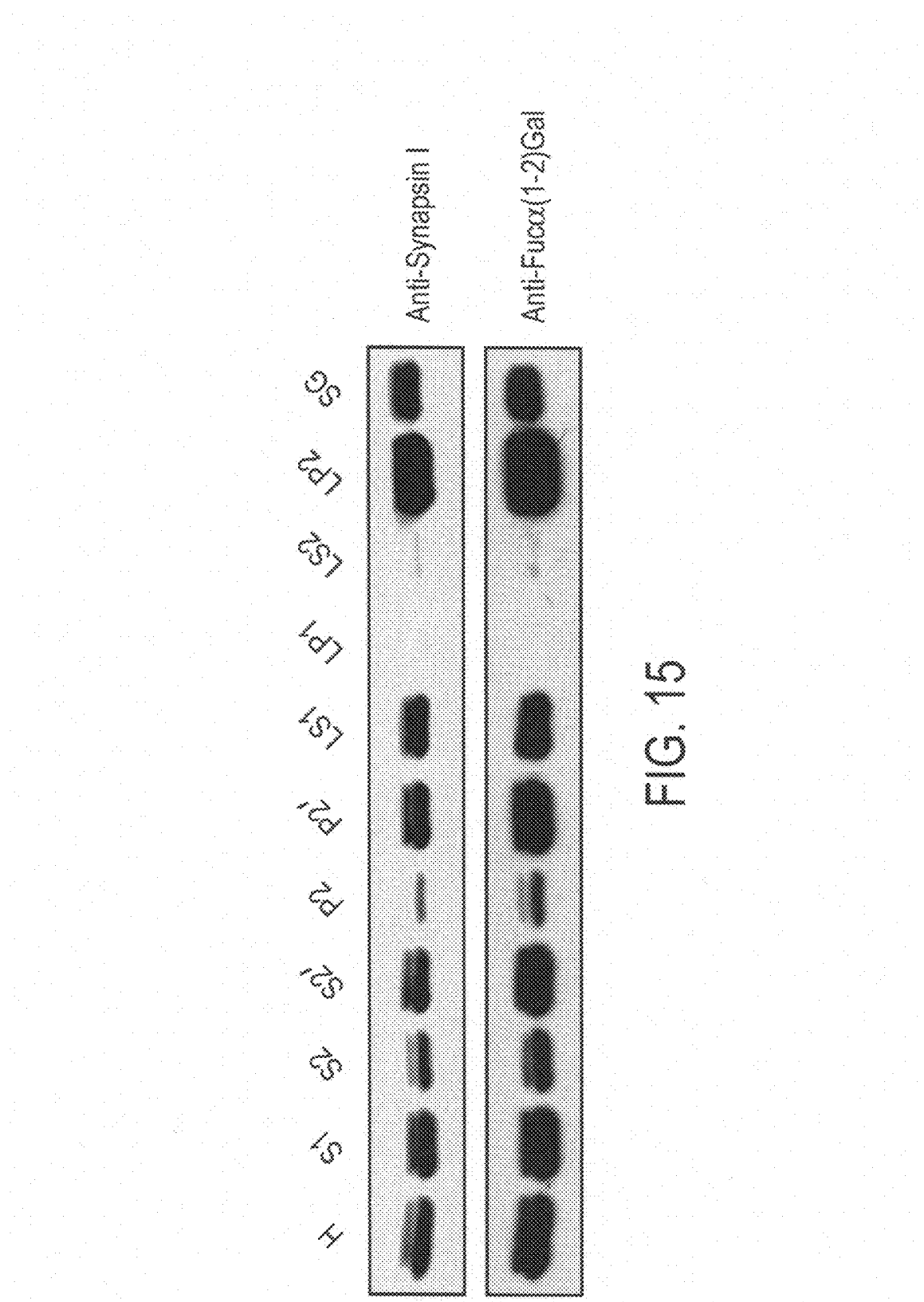
FIG. 15. Distribution of synapsin Ia/Ib and fucosylated synapsin in subcellular fractions of rat forebrain. Protein extracts from the indicated subcellular fractions were immunoblotted with an anti-synapsin I antibody or A46-B/B10. H, homogenate; S1, postnuclear supernatant; S2, supernatant of P2; P2, crude synaptosomes; LS1, supernatant of LP1; LP1, crude synaptic plasma membranes; LS2, supernatant of LP2 (synaptosol); LP2, crude synaptic vesicles; SG, synaptic vesicles after sucrose gradient. Each lane contains 100 μg of protein, with the exception of the SG fraction, which has 10 μg.

The synapsins play essential roles in neurotransmitter release by tethering synaptic vesicles to each other and to the actin cytoskeleton (Hilfiker, S., et al., *Phil. Trans. R. Soc. Lond. B.*, 354:269-279 (1999)). Phosphorylation of synapsin has been shown to serve as a dynamic switch to control the association of synapsin with synaptic vesicles as well as synaptic vesicle dynamics in both mature and developing neurons (Sudhof, T. C., et al., *Science* 245:1474-1480 (1989); Vallorta, F., et al., *Eur. J. Neurosci.* 7:261-270 (1995); Ryan, T. A., et al., *J. Cell Biol.* 134:1219-1227 (1996)). It was therefore investigated whether fucosylation might affect the association of synapsin with synaptic vesicles. Subcellular fractionation of rat forebrain lysates was performed and the resulting fractions analyzed for the levels of fucosylated or total synapsin (FIG. 15; H, homogenate; S1, postnuclear supernatant; S2, supernatant of P2; P2, crude synaptosomes; LS1, supernatant of LP1; LP1, crude synaptic plasma membranes; LS2, supernatant of LP2 (synaptosol); LP2, crude synaptic vesicles; SG, synaptic vesicles after sucrose gradient).

As shown previously, synapsin I was enriched in fractions containing synaptic vesicles (Hunter, W. B., et al., *J. Cell Biol.* 96:1374-1388 (1983); Kao, H. T., et al., *Proc. Natl. Acad. Sci. USA* 95:4667-4672 (1998)). The levels of fucosylated synapsin were equivalent to synapsin expression levels in all subcellular fractions examined. Quantitative analysis revealed that the membrane-associated to soluble ratio (LP2: LS2) of fucosylated synapsin was similar to that of synapsin (~39:1 and 38:1 for fucosylated synapsin and synapsin, respectively). These results suggest that both the membrane-associated and soluble forms of synapsin are fucosylated and that fucosylation does not influence the subcellular localization of synapsin.

To determine the extent of fucosylation on synapsin, we compared the relative binding of antibody A46-B/B10 to purified bovine synapsin I versus a fucosylated bovine serum albumin (BSA) standard (FIG. 15). 2'-Fucosyllactose (Fucα(1-2)Galβ(1-4)GlcNAc) was conjugated to BSA using reductive amination chemistry to afford an epitope density of approximately 3.0±0.8 moles of fucose per BSA molecule. Bovine serum albumin (7.5 nmol, Pierce) was conjugated to 2'fucosyllactose (750 nmol, Glykotech) in 0.2 M borate buffer pH 8.0/100 mM NaCl containing 1 mg sodium cyanoborohydride. The reaction was incubated at 37° C. for 48 h. After dialysis into PBS, the protein concentration was determined by the BCA assay (Pierce). Free lysine content was determined using the Habeeb assay (Wegmann, B., et al., Carbohydr. Res. 184:254-261 (1988)). Briefly, conjugated BSA in PBS (10 μg in 50 μL) was incubated with 0.1% aqueous picrylsulfonic acid (50 μL; Spectrum Chemicals) and 4% NaHCO$_3$, pH 9.5 (50 μL) at 40° C. for 2 h. The reaction was quenched by the addition of 10% SDS (50 μL) and 1M HCl (25 μL). Absorbance values were measured at 363 nm and compared to unconjugated BSA.

Figure 16:
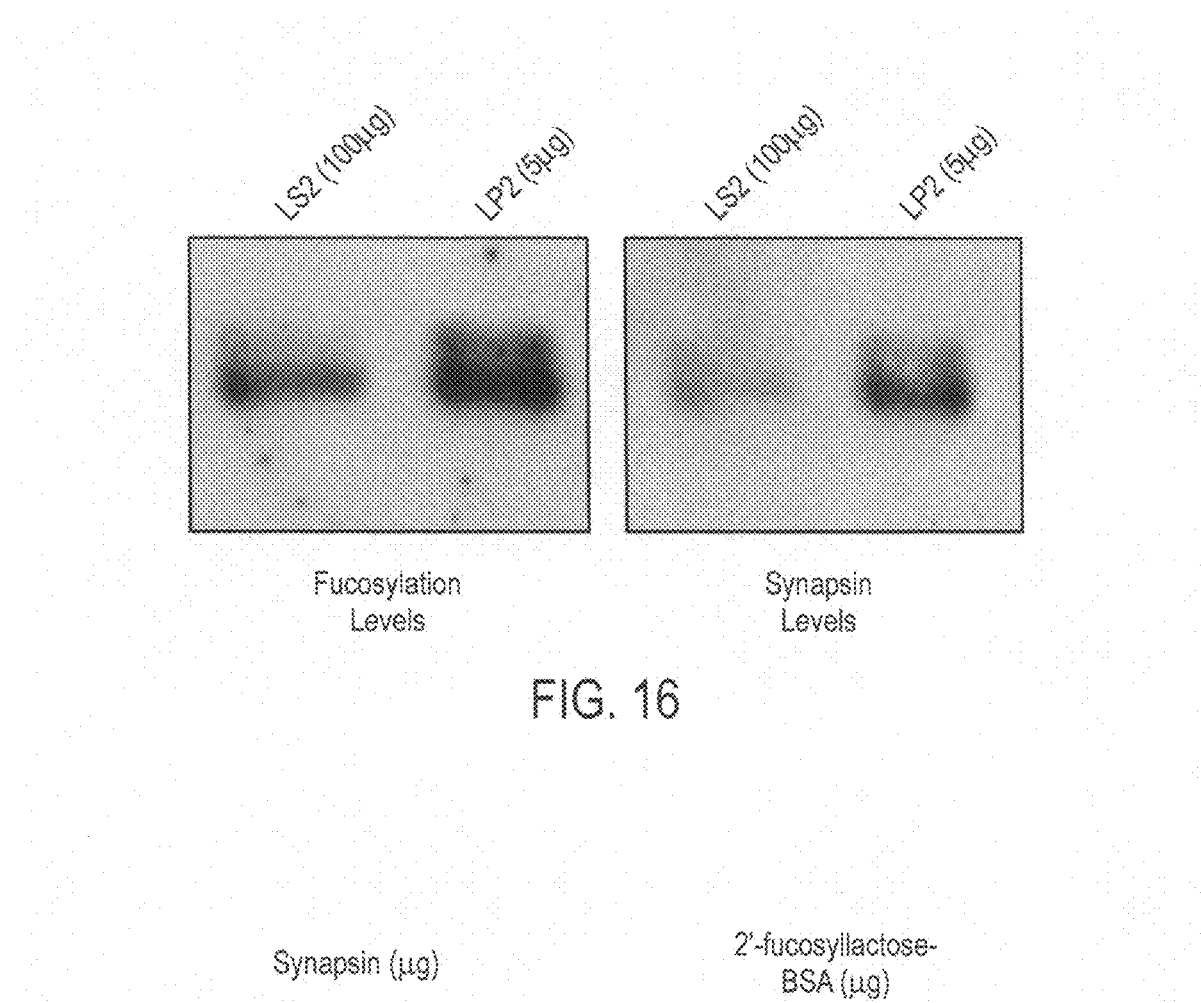
FIG. 16. Comparison of the membrane-associated:soluble ratio of fucosylated synapsin to that of synapsin. The LP2 and LS2 fractions of crude synaptosomes were resolved by SDS-PAGE, and the fucosylation and synapsin levels were measured by immunoblotting with antibody A46-B/B10 and an anti-synapsin antibody, respectively. Quantification was performed using NIH Image software and revealed a similar membrane-associated to soluble ratio (LP2:LS2) for both fucosylated synapsin and synapsin (approximately 39:1 and 38:1 for fucosylated synapsin and synapsin, respectively).
Figure 17:
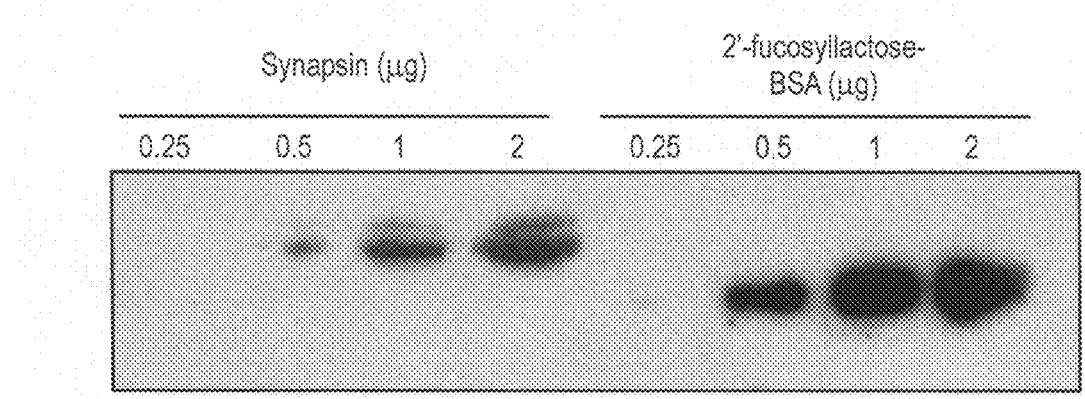
FIG. 17. Quantification of the extent of fucosylation on synapsin I. 2'-Fucosyllactose was conjugated to BSA to afford an epitope density of approximately 3.0±0.8 moles of fucose per BSA molecule. The fucosylation level of the BSA standard was compared to that of purified bovine synapsin I by immunoblotting with antibody A46-B/B10. Quantification was performed by densitometry analysis using NIH Image software and revealed a stoichiometry of approximately 1.5-3.2 Fucα(1-2)Gal epitopes per synapsin molecule.

Western blotting analysis revealed a stoichiometry of approximately 1.5-3.2 Fucα(1-2)Gal epitopes per synapsin molecule (FIGS. 16 and 17), suggesting that a significant fraction of synapsin is fucosylated in the brain. Together with the subcellular fractionation studies, these data show that synapsin fucosylation is pervasive and has a global impact on synapsin function.

Example 10

Inhibiting Synapsin Fucosylation Significantly Decreases its Cellular Half-Life

To investigate further the impact of fucosylation on the functional properties of synapsin, cellular fucosylation of synapsin was inhibited using 2-dGal. 2-dGal has previously been shown to prevent the fucosylation of glycoproteins (Bullock, S., et al., J. Neurochem. 54:135-142 (1990)). Upon cellular uptake, 2-dGal is converted via the Leloir pathway to the corresponding activated uridyl diphosphate (UDP) analog (Id.; Holden, H. M., et al., J. Biol. Chem. 278:43885-43888, (2003)). UDP-2-deoxy-galactose competes with UDP-galactose for incorporation into glycan chains and thereby terminates the chain by preventing formation of the Fucα(1-2)Gal linkage (Bullock, supra).

Figures 18A, 18B:
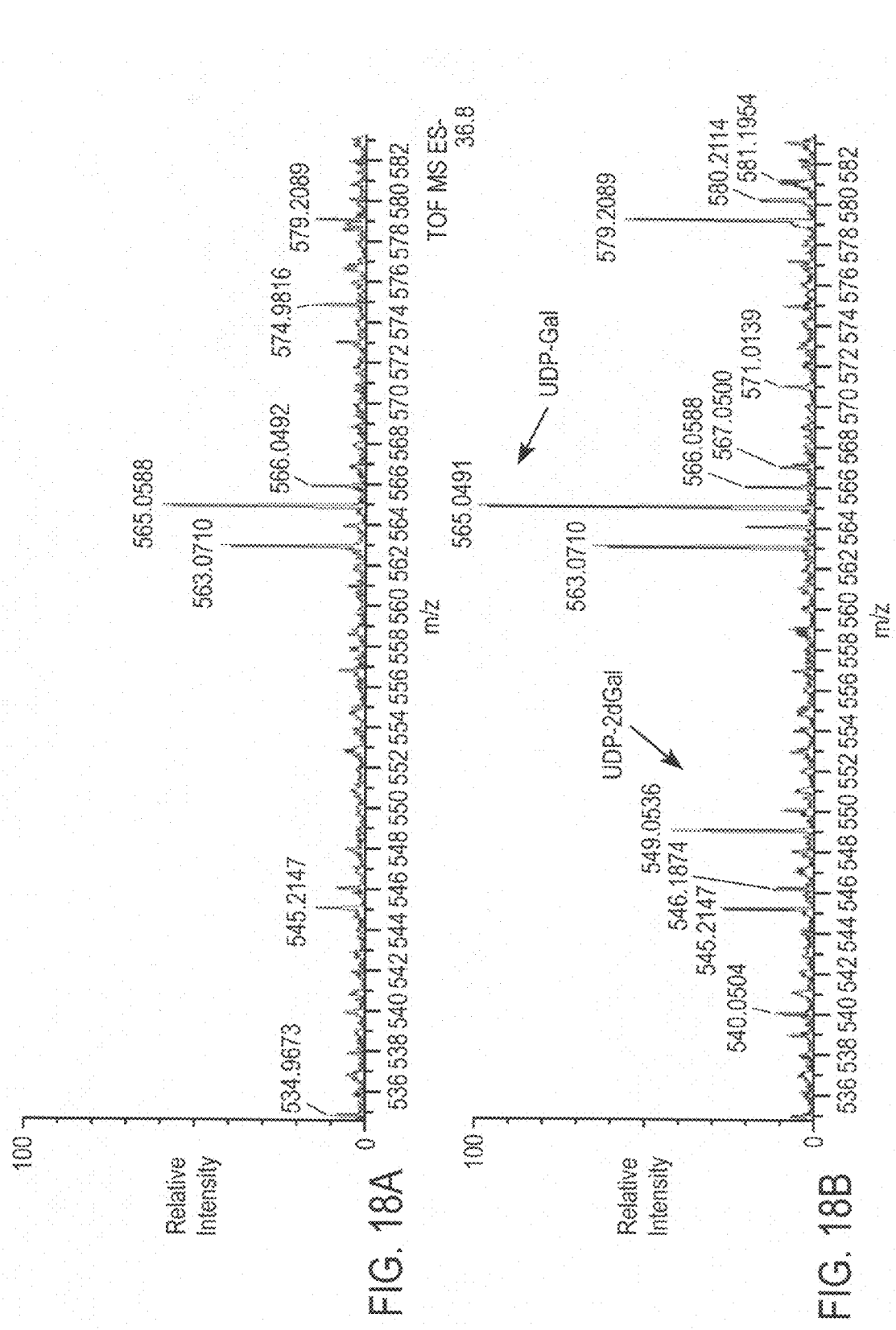
FIG. 18. Treatment of cells with 2-dGal leads to formation of the corresponding UDP analogue, UDP-2dGal. Cells were treated in the absence (A) or presence (B) of 2-dGal, and the extracts were subjected to LC-MS analysis. Significant formation of UDP-2dGal ([M-H]=549.0536, s/n=8:1) was observed upon incubation with 2-dGal (expected m/z=549.0523; 2 ppm).

It was first established that incubation of HeLa cells with 2-dGal leads to the biosynthesis of UDP-2-deoxy-galactose. Significant formation of UDP-2-deoxy-galactose was observed by LC-MS analysis of cell extracts, demonstrating that 2-dGal is an efficient unnatural substrate for the Leloir pathway enzymes (FIG. 18).

The effects of 2-dGal on synapsin I expressed in HeLa cells were next investigated. Cell lysates containing equivalent amounts of transfected protein were resolved by SDS-PAGE, and the fucosylation and protein levels of synapsin were measured by immunoblotting, using methods described above.

19A shows the amount of fucosylation and the amount of synapsin present decreasing at similar rates with the increasing amount of 2d-Gal, while neither the amount of fucosylation or synapsin was affected by the addition of increasing levels of 6 d-Gal. Consistent with the presence of a Fucα(1-2)Gal epitope on synapsin, 2-dGal had a dramatic effect on the fucosylation level of synapsin. The 2-dGal treatment also led to a significant decrease in the level of synapsin protein. These results were specific to 2-dGal, as treatment with another deoxy-galactose sugar, 6-deoxy-D-galactose (6-dGal), had no effect on either the fucosylation or protein levels of synapsin. Thus, 2-dGal was found to affect synapsin levels and fucosylation specifically through the C2 position of galactose.

Example 11

Figure 19A:
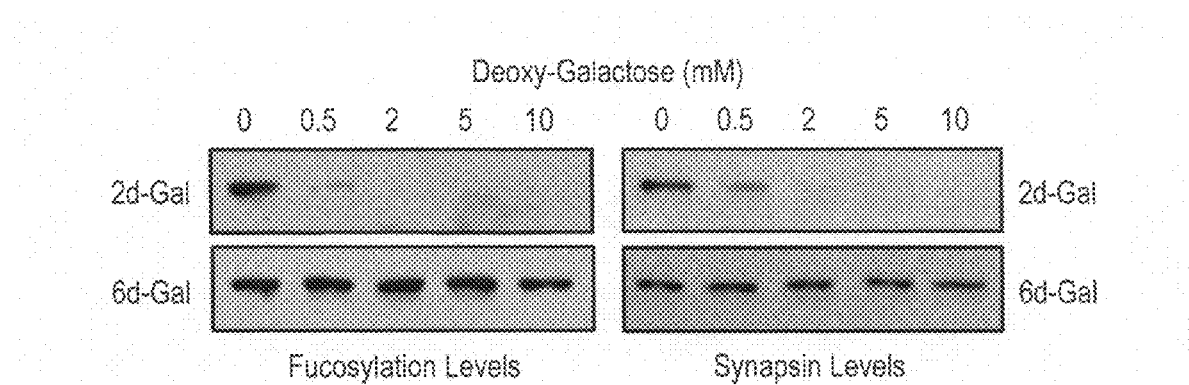
FIG. 19. Inhibition of synapsin fucosylation using 2-dGal decreases the expression and half-life of synapsin I. (A) Effects of 2-dGal and 6-dGal on synapsin fucosylation (left panel) and synapsin expression (right panel) levels. Synapsin I-transfected HeLa cells were treated with the indicated amounts of the deoxy sugar for 24 h. Fucosylation and synapsin expression levels were measured by immunoblotting with antibody A46-B/B10 and an anti-synapsin antibody, respectively. (B) Pulse-chase experiments demonstrate that de-fucosylation significantly decreases the cellular half-life of synapsin from 18 h to 5.5 h. Synapsin I-transfected HeLa cells were treated with 2-dGal or a vehicle control (PBS), pulse labeled with $^{35}$S-L-cysteine and $^{35}$S-L-methionine as described in Materials and Methods, and chased for the indicated times. $^{35}$S-labeled synapsin levels were measured by autoradiography. (C) Inhibition of the calcium-activated protease calpain using a calpain inhibitor peptide or calpeptin protects synapsin from degradation. The lysosomal inhibitors bafilomycin A1 and ammonium chloride and the proteasome inhibitor MG132 had no effect on synapsin degradation. Synapsin I-transfected HeLa cells were treated with the indicated inhibitors or vehicle control (DMSO, PBS or MeOH) in the presence or absence of 2-dGal for 15 h. Following lysis, the cell extracts were analyzed for synapsin expression levels by immunoblotting.
Figure 19B:
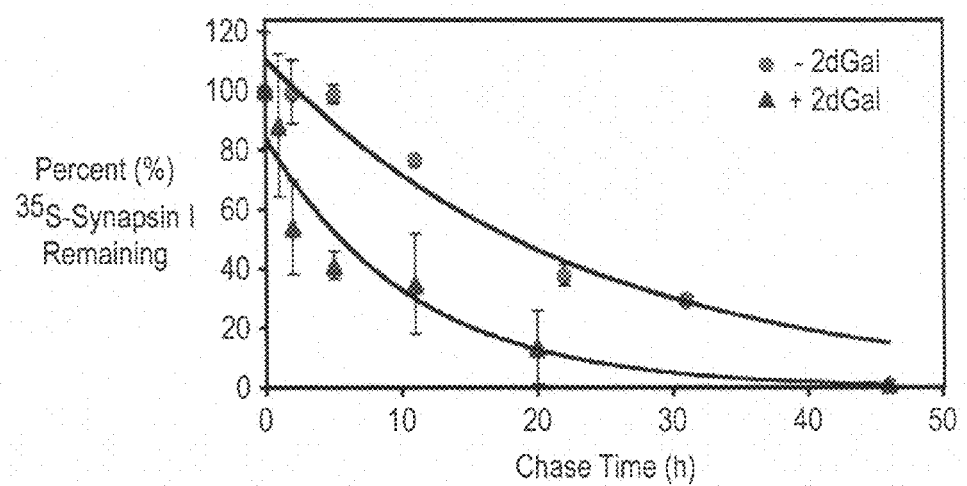

Inhibiting Synapsin Fucosylation Using 2-dGal Significantly Decreases its Half-Life Based on these results, it was postulated that fucosylation might be critical for the half-life and turnover of synapsin in cells. Pulse-chase experiments were conducted, following synapsin Ia expressed in HeLa cells in the presence or absence of 2-dGal. Cells were pulse labeled with $^{35}$S-L-cysteine and $^{35}$S-L-methionine and then incubated for various times in the absence of radioisotopes. After the indicated chase times, synapsin Ia was immunoprecipitated from the cell lysates. A relatively long half-life of 18 h was observed for synapsin Ia (FIG. 19B), consistent with previous studies of endogenous synapsin I in cultured hippocampal neurons ($t_{1/2} \approx 20$ h) (Daly, C., et al., J. Neurosci. 17:2365-2375 (1997)). In contrast, treatment of the cells with 2-dGal led to a dramatic reduction in synapsin Ia half-life to 5.5 h. These results indicate that de-fucosylation promotes the rapid cellular degradation of synapsin.

Example 12

Synapsin Degradation is Mediated by the Calcium-Dependent Protease Calpain

To investigate the molecular mechanisms responsible for synapsin degradation, cells expressing synapsin were treated with various inhibitors of protein degradation in the presence or absence of 2-dGal. Specifically, the lysosomal inhibitors bafilomycin A1 and ammonium chloride, the proteasome inhibitor MG132, and two inhibitors of the calcium-dependent protease calpain, were used.

Figure 19C:
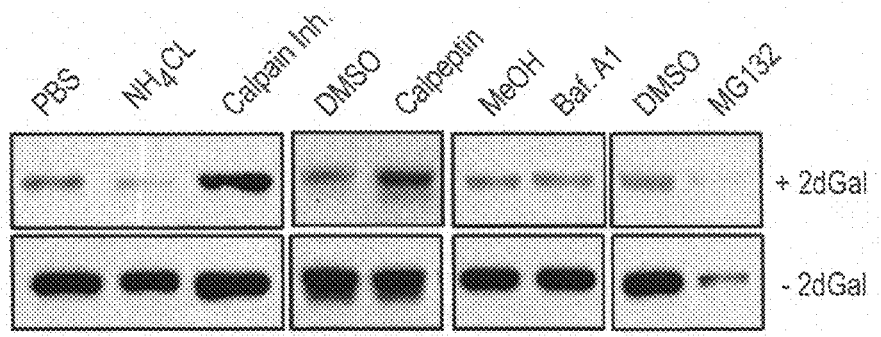

With the exception of MG132, the inhibitors had minimal effects on synapsin expression levels in the absence of 2-dGal (FIG. 19C). As expected, 2-dGal treatment of the cells significantly reduced the levels of synapsin expression. Notably, inhibition of the protease calpain using a calpain inhibitor peptide or calpeptin rescued the effects of 2-dGal, significantly attenuating the loss of synapsin, whereas the lysosomal and proteasomal inhibitors could not rescue synapsin from degradation. These data indicate that fucosylation protects synapsin from rapid degradation mediated, at least in part, by the $Ca^{2+}$-dependent protease calpain.

Example 13

Figure 20A:
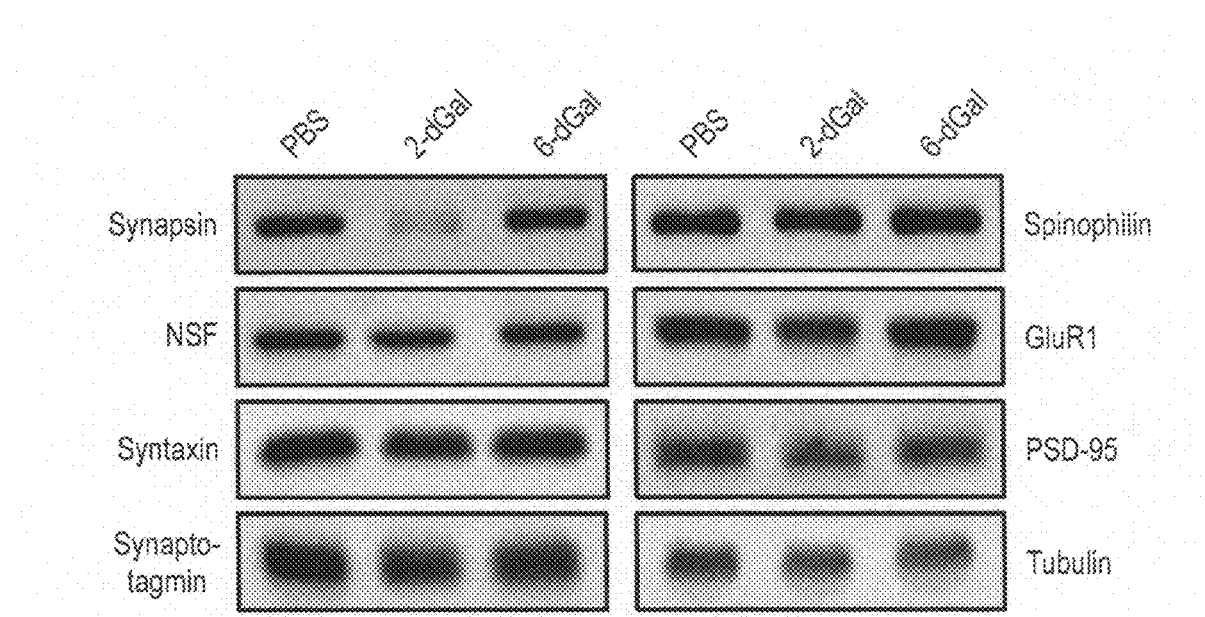
FIG. 20. 2-dGal but not 6-dGal reduces synapsin I expression levels in cultured neurons and induces neurite retraction. (A) E18 cortical neurons cultured for 7 DIV were treated with 15 mM of 2-dGal or 6-dGal for 3 days. Protein lysates were analyzed by Western blotting using antibodies selective for the indicated proteins. A significant reduction in the expression of synapsin Ib was observed, while other synapse-associated proteins were unaffected by the 2-dGal treatment. (B) Neurite retraction caused by 2-dGal is reduced in synapsin-deficient mice. Neurons from synapsin I-deficient or wild-type mice were cultured for 2 days, treated with 2-dGal for 3 days, and analyzed for mean neurite length.

Synapsin Fucosylation Modulates its Expression in Neurons and is Required for Proper Neurite Outgrowth and Synapse Formation To examine the effects of 2-dGal on synapsin fucosylation in neurons, neurons were cultured for 7 DIV to allow for adequate expression of synapsin and subsequently treated with 2-dGal or 6-dGal for comparison. Cells were lysed and immunoblotted as described above. As expected, 2-dGal dramatically reduced the expression of synapsin I in cultured neurons, whereas 6-dGal had no effect (FIG. 20A). The expression of other synaptic proteins, including NSF, the synaptic vesicle protein synaptotagmin, the presynaptic plasma membrane protein syntaxin, and the postsynaptic proteins PSD-95, the AMPA receptor GluR1 subunit and spinophilin, was unchanged by the 2-dGal treatment.

Figure 20B:
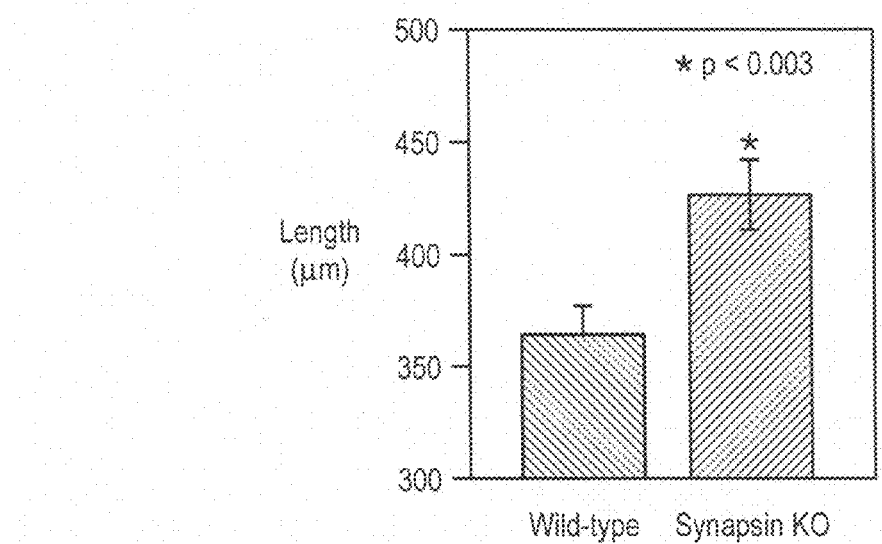

Although synapsin I represents the major fucosylated protein in mature neuronal cultures, other proteins are also covalently modified by Fucα(1-2)Gal during early developmental stages (See FIG. 9A). The relative contribution of synapsin to the striking effects of 2-dGal on neuronal morphology were therefore investigated. Neurons were cultured from synapsin I-deficient (Chin, L. S., et al., *Proc. Natl. Acad. Sci. USA* 92:9230-9234 (1995); Drs. H. T Kao and P. Greengard, The Rockefeller University, New York, N.Y.) or wild-type mice for 2 days, treated with 2-dGal for 3 days, immunostained for tubulin, and examined by confocal fluorescence microscopy. Despite the fact that other fucosylated glycoproteins are prominently expressed along with synapsin in wild-type mice after 5 DIV (FIG. 9A), the 2-dGal-mediated neurite retraction was markedly reduced in the absence of synapsin. The mean neurite length for cultured neurons from synapsin knockout mice was increased by 17.4±5.2% when compared to those of wild-type mice (FIG. 20B; n=50; p<0.003). These data demonstrate that fucosylation of synapsin contributes to neuronal outgrowth and synaptogenesis. The observation that neurite retraction is not completely abolished in the synapsin knockout mice suggests that Fucα(1-2)Gal sugars also modulate other proteins involved in the regulation of neuronal morphology.

Example 14

Delivery of Fucose-Galactose Compounds to the Brain

A patient with idiopathic, bilateral Parkinson's Disease is treated with fucose-galactose compounds directly to the brain, using a procedure modified from Gill, S. S., et al., *Nat. Med.*, 9:589-595 (2003). Full consent in accordance with local ethics committees is obtained for the procedure. The patient is analyzed using a mid-sagittal planning PET scan, producing 2-mm thick axial images parallel to the anterior-posterior plane. Coronal images that are orthogonal to the initial images are produced. The patient is placed under general anesthesia, and a sterotactic frame is placed parallel to the orbito-meatal plane. The images are used to target the area of the postero-dorsal putamen with Fucα(1-2)Gal-PAA polymers (polyacrylamide polymers bearing multiple Fucα(1-2) Gal epitopes) having a density of 30%. 1 mm guide tubes are implanted under sterotaxic conditions to a point above the putamen target over a guide rod. A 0.6 mm guide wire is introduced down the guide tube to the target, and the patient then undergoes repeat magnetic resonance and computed tomography imaging to verify target localization. A Fucα(1-2)Gal-PAA-primed SynchroMed pump (Medtronic, Minneapolis Minn.) is implanted in the upper abdominal region, subfascially (beneath the anterior rectus sheath). A catheter is tunneled connecting the pump to the indwelling 0.6 mm intraparenchymal brain catheter.

FucGal-PAA is supplied preferably at a concentration between about 500 nM and about 1000 mM, to be pumped in sterile water buffered with 10 nM citrate and 150 mM sodium chloride at pH 5.0. After implantation, the SynchroMed pump is programmed to deliver a continuous infusion at a predetermined concentration, preferably between about 500 nM and about 500 mM preferably between about 1 μM and about 500 μM, of Fucα(1-2)Gal-PAA to the putamen per day at a rate of 6 μL/h. Clinical evaluations are performed prior to infusion, at 3 month, at 6 months, at 9 months, and at 12 months, using CAPIT (Langston, J. W., et al., *Mov. Disord.*, 7:2-13 (1992)), studying mobility, activities of daily living, emotional well being, stigma, social support, cognition, communication, and bodily discomfort.

Example 15

Growth of Neural Stem Cells Enhanced With Fucα(1-2)Gal

The compositions of the invention are useful for stimulating the growth of neural stem cells, both in culture and in vivo. For in vivo delivery, a composition of Fucα(1-2)Gal in water or phosphate buffered saline is added to the neural stem cell medium at a concentration between about 50 nM to about 500 mM, preferably between about 1 μM and about 500 μM, at the time of transplantation into the desired location in a mammalian subject.

To improve the in vitro culture of neural stem cells or progenitor cells, the cells are cultured using a modified method of Schwartz, et al., supra. All procedures are performed in a sterile class II biosafety hood. Crude homogenates of tissue are derived from pathogen-negative mammalian cortex and plated in primary growth medium composed of high glucose 1:1 DMEM:F12 (Irvine Scientific, Irvine, Calif.), supplemented with 10% heat-inactivated fetal bovine serum, 10% BIT 9500 (Stem Cell Technologies), 40 ng/ml basic FGF-2 (Invitrogen), 20 ng/mL EGF (Invitrogen), and 20 ng/mL PDGF-AB (Peprotech) on fibronectin-coated dishes that have previously been conditioned by incubating with 200 μL/cm$^2$ of fibronectin (5 μL/ml; Sigma) overnight at 37° C., aspirated, and air dried. Nonadherent cells and debris are transferred to a new set of fibronectin-coated culture dishes after pelleting, and are cultured in fresh serum-free medium, and Fucα(1-2)Gal-PAA (30% density) is added at about the same concentration as previously used, with 50% of the medium plus Fucα(1-2)Gal composition being changed daily.

Example 16

Improving Engineered Mammalian Tissue Using Fucα(1-2)Gal

To provide a skin graft, a modified version of the procedure of Horch, Raymond E., et al., *Tissue Engineering*, 6:53-67 (2000) is used. Proliferative human keratinocytes are isolated from abundant fresh human skin from plastic surgical procedures with 0.25% Dispase (Boehringer, Mannheim, Germany) after incubation at 40° C. over 2 h. Epidermal cells are then isolated into a single cell suspension by treatment with 0.05% trypsin and 0.02% EDTA (Invitrogen) at 37° C. for 30 min, resuspended and expanded in number in 75 cm$^2$ polystyrene tissue culture flasks in serum-free media containing EGF, BPE (Invitrogen), and gentamycin (Merck, Germany) at 5% CO$_2$ and 37° C. At 60-70% subconfluence, the cells are harvested from the flasks by trypsinization and are reincubated in a concentration of 1×10$^6$ per 75 cm$^2$ culture flask.

The collagen membrane consists of 4 mg of highly purified native type 1 bovine collagen per cm$^2$ and is translucent. By a specific manufacturing process, chemical cross-linking is prevented. The elasticity and pliability of the collagen membrane can be maintained for a period of 3 weeks or more after the material had been submerged in culture medium under culture conditions.

Second passage keratinocytes are isolated into a single cell suspension upon reaching subconfluence of 60-70% in the culture flasks. Cells are then inoculated onto a commercially available bovine collagen type 1 membrane (TissuFascie®, Baxter-Immuno, Germany) at a density of 100,000 cells per $cm^2$ and are submerged in culture medium for 3-5 days until subconfluence is reached on the membranes. Fucα(1-2)Gal-PAA is present in the media during incubation.

We claim:

1. A method for inducing neuronal outgrowth comprising the steps of administering to a neuron a composition comprising: a Fucoseα(1-2) galactose (fucα(1-2)gal) moiety, a lectin that selectively binds to a fucα(1-2)gal moiety, or a combination of a fucα(1-2)gal moiety and a UEA-1 lectin or a LTL lectin.

2. The method of claim 1 wherein the fucα(1-2)gal moiety is attached to a polymer.

3. The method of claim 2 wherein the polymer is selected from polyacrylamide, polyethylene glycol, polypropylene glycol, and combinations thereof.

4. A method of growing neural stem cells comprising the addition to the growth media of a composition comprising: a Fucoseα(1-2) galactose (fucα(1-2)gal) moiety, a lectin that selectively binds to a fucα(1-2)gal moiety or a combination of a fucα(1-2)gal moiety and a UEA-1 lectin or a LTL lectin.

5. The method of claim 4 wherein the fucose-galactose moiety is attached to a polymer.

6. The method of claim 5 wherein the polymer is selected from polyacrylamide, polyethylene glycol, polypropylene glycol, and combinations thereof.

* * * * *

UNITED STATES PATENT AND TRADEMARK OFFICE
CERTIFICATE OF CORRECTION

PATENT NO. : 7,858,578 B2  Page 1 of 1
APPLICATION NO. : 11/297165
DATED : December 28, 2010
INVENTOR(S) : Stacey Kalovidouris It is certified that error appears in the above-identified patent and that said Letters Patent is hereby corrected as shown below:

In the Claims

In column 29, line 9, the words "the steps of" should be deleted.

Signed and Sealed this
Twenty-first Day of June, 2011

David J. Kappos
*Director of the United States Patent and Trademark Office*